(12) United States Patent
Demmer et al.

(10) Patent No.: US 9,724,519 B2
(45) Date of Patent: Aug. 8, 2017

(54) VENTRICULAR LEADLESS PACING DEVICE MODE SWITCHING

(71) Applicant: Medtronic, Inc., Minneapolis, MN (US)

(72) Inventors: Wade M Demmer, Coon Rapids, MN (US); Todd J Sheldon, Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 128 days.

(21) Appl. No.: 14/694,976

(22) Filed: Apr. 23, 2015

(65) Prior Publication Data
US 2016/0129261 A1 May 12, 2016

Related U.S. Application Data

(63) Continuation-in-part of application No. 14/538,486, filed on Nov. 11, 2014, now Pat. No. 9,492,669, and
(Continued)

(51) Int. Cl.
*A61N 1/362* (2006.01)
*A61N 1/365* (2006.01)
(Continued)

(52) U.S. Cl.
CPC ....... *A61N 1/36585* (2013.01); *A61N 1/3688* (2013.01); *A61N 1/3756* (2013.01); *A61N 1/37205* (2013.01)

(58) Field of Classification Search
CPC . A61N 1/3688; A61N 1/37205; A61N 1/3756
See application file for complete search history.

(56) References Cited

U.S. PATENT DOCUMENTS 3,486,506 A  12/1969 Auphan
3,659,615 A  5/1972  Enger
(Continued)

FOREIGN PATENT DOCUMENTS

CN  101185789 A  5/2008
CN  101284160 A  10/2008
(Continued)

OTHER PUBLICATIONS

US 8,116,861, 02/2012, Root et al. (withdrawn)
(Continued)

*Primary Examiner* — George Evanisko

(57) ABSTRACT

In some examples, a leadless pacing device (LPD) is configured to switch from a sensing without pacing mode to ventricular pacing mode in response to determining that no intrinsic ventricular activity was detected within a ventricular event detection window for at least one cardiac cycle, which may be referred to as loss of conduction. The ventricular pacing mode may be selected based on whether atrial oversensing is detected in combination with the loss of conduction. In some examples, an atrio-ventricular synchronous pacing mode is selected in response to detecting loss of conduction and in response to determining that atrial oversensing is not detected. In addition, in some examples, an asynchronous ventricular pacing mode is selected in response to detecting both atrial oversensing and loss of conduction.

52 Claims, 13 Drawing Sheets

Related U.S. Application Data a continuation-in-part of application No. 14/538,518, filed on Nov. 11, 2014, now Pat. No. 9,492,668.

(51) Int. Cl.
*A61N 1/375* (2006.01)
*A61N 1/372* (2006.01)
*A61N 1/368* (2006.01)

(56) References Cited

U.S. PATENT DOCUMENTS

| | | |
|---|---|---|
| 3,693,625 A | 9/1972 | Auphan |
| 3,835,864 A | 9/1974 | Rasor et al. |
| 3,943,936 A | 3/1976 | Rasor et al. |
| 4,157,720 A | 6/1979 | Greatbatch |
| RE30,366 E | 8/1980 | Rasor et al. |
| 4,256,115 A | 3/1981 | Bilitch |
| 4,333,469 A | 6/1982 | Jeffcoat et al. |
| 5,144,949 A | 9/1992 | Olson |
| 5,170,784 A | 12/1992 | Ramon et al. |
| 5,193,539 A | 3/1993 | Schulman et al. |
| 5,193,540 A | 3/1993 | Schulman et al. |
| 5,243,977 A | 9/1993 | Trabucco et al. |
| 5,312,439 A | 5/1994 | Loeb |
| 5,324,316 A | 6/1994 | Schulman et al. |
| 5,391,189 A | 2/1995 | van Krieken et al. |
| 5,404,877 A | 4/1995 | Nolan et al. |
| 5,405,367 A | 4/1995 | Schulman et al. |
| 5,411,535 A | 5/1995 | Fujii et al. |
| 5,441,527 A | 8/1995 | Erickson et al. |
| 5,454,836 A | 10/1995 | van der Veen et al. |
| 5,540,728 A | 7/1996 | Shelton et al. |
| 5,674,259 A | 10/1997 | Gray |
| 5,792,208 A | 8/1998 | Gray |
| 5,814,089 A | 9/1998 | Stokes et al. |
| 5,843,132 A | 12/1998 | Ilvento |
| 5,893,882 A | 4/1999 | Peterson et al. |
| 5,895,414 A | 4/1999 | Sanchez-Zambrano |
| 5,954,757 A | 9/1999 | Gray |
| 5,970,986 A | 10/1999 | Bolz et al. |
| 5,987,352 A | 11/1999 | Klein et al. |
| 6,044,300 A | 3/2000 | Gray |
| 6,051,017 A | 4/2000 | Loeb et al. |
| 6,129,745 A | 10/2000 | Sun et al. |
| 6,141,588 A | 10/2000 | Cox et al. |
| 6,144,879 A | 11/2000 | Gray et al. |
| 6,175,764 B1 | 1/2001 | Loeb et al. |
| 6,181,965 B1 | 1/2001 | Loeb et al. |
| 6,185,452 B1 | 2/2001 | Schulman et al. |
| 6,185,455 B1 | 2/2001 | Loeb et al. |
| 6,208,894 B1 | 3/2001 | Schulman et al. |
| 6,214,032 B1 | 4/2001 | Loeb et al. |
| 6,240,316 B1 | 5/2001 | Richmond et al. |
| 6,315,721 B2 | 11/2001 | Schulman et al. |
| 6,321,115 B1 | 11/2001 | Mouchawar et al. |
| 6,415,184 B1 | 7/2002 | Ishikawa et al. |
| 6,434,424 B1 | 8/2002 | Igel et al. |
| 6,445,953 B1 | 9/2002 | Bulkes et al. |
| 6,477,420 B1 | 11/2002 | Stuble et al. |
| 6,592,518 B2 | 7/2003 | Denker et al. |
| 6,628,989 B1 | 9/2003 | Penner et al. |
| 6,654,638 B1 | 11/2003 | Sweeny |
| 6,733,485 B1 | 5/2004 | Whitehurst et al. |
| 6,735,474 B1 | 5/2004 | Loeb et al. |
| 6,735,475 B1 | 5/2004 | Whitehurst et al. |
| 6,738,672 B2 | 5/2004 | Schulman et al. |
| 6,764,446 B2 | 7/2004 | Wolinsky et al. |
| 6,788,975 B1 | 9/2004 | Whitehurst et al. |
| 6,804,561 B2 | 10/2004 | Stover |
| 6,819,955 B2 | 11/2004 | Levine |
| 6,871,099 B1 | 3/2005 | Whitehurst et al. |
| 6,904,315 B2 | 6/2005 | Panken et al. |
| 6,907,285 B2 | 6/2005 | Denker et al. |
| 6,917,833 B2 | 7/2005 | Denker et al. |
| 6,941,171 B2 | 9/2005 | Mann et al. |
| 6,947,782 B2 | 9/2005 | Schulman et al. |
| 7,003,350 B2 | 2/2006 | Denker et al. |
| 7,006,864 B2 | 2/2006 | Echt et al. |
| 7,024,248 B2 | 4/2006 | Penner et al. |
| 7,050,849 B2 | 5/2006 | Echt et al. |
| 7,054,692 B1 | 5/2006 | Whitehurst et al. |
| 7,082,336 B2 | 7/2006 | Ransbury et al. |
| 7,103,408 B2 | 9/2006 | Haller et al. |
| 7,114,502 B2 | 10/2006 | Schulman et al. |
| 7,120,992 B2 | 10/2006 | He et al. |
| 7,132,173 B2 | 11/2006 | Daulton |
| 7,167,751 B1 | 1/2007 | Whitehurst et al. |
| 7,177,698 B2 | 2/2007 | Klosterman et al. |
| 7,184,830 B2 | 2/2007 | Echt et al. |
| 7,198,603 B2 | 4/2007 | Penner et al. |
| 7,200,437 B1 | 4/2007 | Nabutovsky et al. |
| 7,203,548 B2 | 4/2007 | Whitehurst et al. |
| 7,214,189 B2 | 5/2007 | Zdeblick |
| 7,236,821 B2 | 6/2007 | Cates et al. |
| 7,236,829 B1 | 6/2007 | Farazi et al. |
| 7,260,436 B2 | 8/2007 | Kilgore et al. |
| 7,283,874 B2 | 10/2007 | Penner |
| 7,286,883 B2 | 10/2007 | Schulman et al. |
| 7,292,890 B2 | 11/2007 | Whitehurst et al. |
| 7,294,108 B1 | 11/2007 | Bornzin et al. |
| 7,295,879 B2 | 11/2007 | Denker et al. |
| 7,310,556 B2 | 12/2007 | Bulkes |
| 7,330,756 B2 | 2/2008 | Marnfeldt |
| 7,343,204 B2 | 3/2008 | Schulman et al. |
| 7,351,921 B1 | 4/2008 | Haller et al. |
| 7,363,082 B2 | 4/2008 | Ransbury et al. |
| 7,376,461 B2 | 5/2008 | Perschbacher et al. |
| 7,428,438 B2 | 9/2008 | Parramon et al. |
| 7,437,193 B2 | 10/2008 | Parramon et al. |
| 7,444,180 B2 | 10/2008 | Kuzma et al. |
| 7,450,998 B2 | 11/2008 | Zilberman et al. |
| 7,493,172 B2 | 2/2009 | Whitehurst et al. |
| 7,513,257 B2 | 4/2009 | Schulman et al. |
| 7,519,421 B2 | 4/2009 | Denker et al. |
| 7,519,424 B2 | 4/2009 | Dennis et al. |
| 7,529,589 B2 | 5/2009 | Williams et al. |
| 7,532,932 B2 | 5/2009 | Denker et al. |
| 7,532,933 B2 | 5/2009 | Hastings et al. |
| 7,535,296 B2 | 5/2009 | Bulkes et al. |
| 7,555,345 B2 | 6/2009 | Wahlstrand et al. |
| 7,558,631 B2 | 7/2009 | Cowan et al. |
| 7,565,195 B1 | 7/2009 | Kroll et al. |
| 7,587,241 B2 | 9/2009 | Parramon et al. |
| 7,606,621 B2 | 10/2009 | Brisken et al. |
| 7,610,092 B2 | 10/2009 | Cowan et al. |
| 7,616,990 B2 | 11/2009 | Chavan et al. |
| 7,616,992 B2 | 11/2009 | Dennis et al. |
| 7,617,007 B2 | 11/2009 | Williams et al. |
| 7,627,371 B2 | 12/2009 | Wang et al. |
| 7,627,376 B2 | 12/2009 | Dennis et al. |
| 7,627,383 B2 | 12/2009 | Haller et al. |
| 7,630,767 B1 | 12/2009 | Poore et al. |
| 7,634,313 B1 | 12/2009 | Kroll et al. |
| 7,637,867 B2 | 12/2009 | Zdeblick |
| 7,640,060 B2 | 12/2009 | Zdeblick |
| 7,640,061 B2 | 12/2009 | He et al. |
| 7,647,109 B2 | 1/2010 | Hastings et al. |
| 7,650,186 B2 | 1/2010 | Hastings et al. |
| 7,706,892 B2 | 4/2010 | Colvin et al. |
| 7,713,194 B2 | 5/2010 | Zdeblick |
| 7,734,343 B2 | 6/2010 | Ransbury et al. |
| 7,747,335 B2 | 6/2010 | Williams |
| 7,751,881 B2 | 7/2010 | Cowan et al. |
| 7,766,216 B2 | 8/2010 | Daulton |
| 7,771,838 B1 | 8/2010 | He et al. |
| 7,781,683 B2 | 8/2010 | Haller et al. |
| 7,797,045 B2 | 9/2010 | Amblard |
| 7,809,438 B2 | 10/2010 | Echt et al. |
| 7,822,480 B2 | 10/2010 | Park et al. |
| 7,826,903 B2 | 11/2010 | Denker et al. |
| 7,840,282 B2 | 11/2010 | Williams et al. |
| 7,848,815 B2 | 12/2010 | Brisken et al. |
| 7,848,823 B2 | 12/2010 | Drasler et al. |
| 7,860,564 B2 | 12/2010 | Root et al. |

(56) References Cited

U.S. PATENT DOCUMENTS

| | | |
|---|---|---|
| 7,860,570 B2 | 12/2010 | Whitehurst et al. |
| 7,890,173 B2 | 2/2011 | Brisken et al. |
| 7,894,907 B2 | 2/2011 | Cowan et al. |
| 7,899,541 B2 | 3/2011 | Cowan et al. |
| 7,899,542 B2 | 3/2011 | Cowan et al. |
| 7,899,554 B2 | 3/2011 | Williams et al. |
| 7,904,167 B2 | 3/2011 | Klosterman et al. |
| 7,930,031 B2 | 4/2011 | Penner |
| 7,937,148 B2 | 5/2011 | Jacobson |
| 7,945,333 B2 | 5/2011 | Jacobson |
| 7,957,805 B2 | 6/2011 | He |
| 7,979,126 B2 | 7/2011 | Payne et al. |
| 7,991,467 B2 | 8/2011 | Markowitz et al. |
| 7,996,097 B2 | 8/2011 | DiBernardo et al. |
| 8,010,209 B2 | 8/2011 | Jacobson |
| 8,019,419 B1 | 9/2011 | Panescu et al. |
| 8,032,219 B2 | 10/2011 | Neumann et al. |
| 8,032,227 B2 | 10/2011 | Parramon et al. |
| 8,078,279 B2 | 12/2011 | Dennis et al. |
| 8,078,283 B2 | 12/2011 | Cowan et al. |
| 8,116,883 B2 | 2/2012 | Williams et al. |
| 8,126,561 B2 | 2/2012 | Chavan et al. |
| 8,127,424 B2 | 3/2012 | Haller et al. |
| 8,165,696 B2 | 4/2012 | McClure et al. |
| 8,185,212 B2 | 5/2012 | Carbunaru et al. |
| 8,204,595 B2 | 6/2012 | Pianca et al. |
| 8,224,449 B2 | 7/2012 | Carbunaru et al. |
| 8,237,992 B2 | 8/2012 | Hiramatsu |
| 8,239,045 B2 | 8/2012 | Ransbury et al. |
| 8,240,780 B1 | 8/2012 | Klimes |
| 8,295,939 B2 | 10/2012 | Jacobson |
| 8,301,242 B2 | 10/2012 | Root et al. |
| 8,301,262 B2 | 10/2012 | Mi et al. |
| 8,311,627 B2 | 11/2012 | Root et al. |
| 8,315,701 B2 | 11/2012 | Cowan et al. |
| 8,321,036 B2 | 11/2012 | Brockway et al. |
| 8,332,036 B2 | 12/2012 | Hastings et al. |
| 8,340,780 B2 | 12/2012 | Hastings et al. |
| 8,352,025 B2 | 1/2013 | Jacobson |
| 8,352,028 B2 | 1/2013 | Wenger |
| 8,359,098 B2 | 1/2013 | Lund et al. |
| 8,364,267 B2 | 1/2013 | Schleicher et al. |
| 8,364,276 B2 | 1/2013 | Willis |
| 8,364,278 B2 | 1/2013 | Pianca et al. |
| 8,364,280 B2 | 1/2013 | Marnfeldt et al. |
| 8,368,051 B2 | 2/2013 | Ting et al. |
| 8,374,696 B2 | 2/2013 | Sanchez et al. |
| 8,386,051 B2 | 2/2013 | Rys |
| 8,457,742 B2 | 6/2013 | Jacobson |
| 8,478,408 B2 | 7/2013 | Hastings et al. |
| 8,478,431 B2 | 7/2013 | Griswold et al. |
| 8,489,205 B2 | 7/2013 | Stotts et al. |
| 8,494,637 B2 | 7/2013 | Cowan et al. |
| 8,494,642 B2 | 7/2013 | Cowan et al. |
| 8,494,644 B2 | 7/2013 | Cowan et al. |
| 8,504,156 B2 | 8/2013 | Bonner et al. |
| 8,527,068 B2 | 9/2013 | Ostroff |
| 8,532,790 B2 | 9/2013 | Griswold |
| 8,541,131 B2 | 9/2013 | Lund et al. |
| 8,543,190 B2 | 9/2013 | Wasson et al. |
| 8,543,204 B2 | 9/2013 | Demmer et al. |
| 8,543,205 B2 | 9/2013 | Ostroff |
| 8,543,216 B2 | 9/2013 | Carbunaru et al. |
| 8,548,605 B2 | 10/2013 | Ollivier |
| 8,560,892 B2 | 10/2013 | Nicholes |
| 8,565,897 B2 | 10/2013 | Regnier et al. |
| 8,588,926 B2 | 11/2013 | Moore et al. |
| 8,626,294 B2 | 1/2014 | Sheldon et al. |
| 8,634,912 B2 | 1/2014 | Bornzin et al. |
| 8,634,919 B1 | 1/2014 | Hou et al. |
| 8,639,335 B2 | 1/2014 | Peichel et al. |
| 8,639,336 B2 | 1/2014 | Bornzin et al. |
| 8,644,922 B2 | 2/2014 | Root et al. |
| 8,660,660 B2 | 2/2014 | Dai et al. |
| 8,670,842 B1 | 3/2014 | Bornzin et al. |
| 8,750,976 B2 | 6/2014 | Stadler et al. |
| 2002/0183794 A1 | 12/2002 | Struble |
| 2003/0078627 A1 | 4/2003 | Casavant et al. |
| 2003/0114905 A1 | 6/2003 | Kuzma |
| 2003/0125777 A1 | 7/2003 | Ding et al. |
| 2003/0204208 A1 | 10/2003 | Kramm |
| 2004/0015204 A1 | 1/2004 | Whitehurst et al. |
| 2004/0073267 A1 | 4/2004 | Holzer |
| 2004/0093039 A1 | 5/2004 | Schumert |
| 2004/0122477 A1 | 6/2004 | Whitehurst et al. |
| 2004/0133242 A1 | 7/2004 | Chapman et al. |
| 2004/0143299 A1 | 7/2004 | Casavant et al. |
| 2004/0147973 A1 | 7/2004 | Hauser |
| 2004/0162590 A1 | 8/2004 | Whitehurst et al. |
| 2004/0172089 A1 | 9/2004 | Whitehurst et al. |
| 2005/0055061 A1 | 3/2005 | Holzer |
| 2005/0070962 A1 | 3/2005 | Echt et al. |
| 2005/0256549 A1 | 11/2005 | Holzer |
| 2005/0288717 A1 | 12/2005 | Sunagawa |
| 2006/0074449 A1 | 4/2006 | Denker et al. |
| 2006/0135999 A1 | 6/2006 | Bodner et al. |
| 2006/0136005 A1 | 6/2006 | Brisken et al. |
| 2006/0173497 A1 | 8/2006 | Mech et al. |
| 2006/0241705 A1 | 10/2006 | Neumann et al. |
| 2006/0241732 A1 | 10/2006 | Denker et al. |
| 2007/0027508 A1 | 2/2007 | Cowan et al. |
| 2007/0060961 A1 | 3/2007 | Echt et al. |
| 2007/0073353 A1 | 3/2007 | Rooney et al. |
| 2007/0075905 A1 | 4/2007 | Denker et al. |
| 2007/0078490 A1 | 4/2007 | Cowan et al. |
| 2007/0088396 A1 | 4/2007 | Jacobson |
| 2007/0088397 A1 | 4/2007 | Jacobson |
| 2007/0106332 A1 | 5/2007 | Denker et al. |
| 2007/0106357 A1 | 5/2007 | Denker et al. |
| 2007/0118187 A1 | 5/2007 | Denker et al. |
| 2007/0129773 A1 | 6/2007 | Bulkes |
| 2007/0135850 A1 | 6/2007 | Amblard |
| 2007/0135883 A1 | 6/2007 | Drasler et al. |
| 2007/0150037 A1 | 6/2007 | Hastings et al. |
| 2007/0156204 A1 | 7/2007 | Denker et al. |
| 2007/0185538 A1 | 8/2007 | Denker et al. |
| 2007/0210862 A1 | 9/2007 | Denker et al. |
| 2007/0219590 A1 | 9/2007 | Hastings et al. |
| 2007/0276444 A1 | 11/2007 | Gelbart et al. |
| 2007/0288076 A1 | 12/2007 | Bulkes et al. |
| 2007/0288077 A1 | 12/2007 | Bulkes et al. |
| 2007/0293904 A1 | 12/2007 | Gelbart et al. |
| 2007/0293908 A1 | 12/2007 | Cowan et al. |
| 2007/0293912 A1 | 12/2007 | Cowan et al. |
| 2007/0293913 A1 | 12/2007 | Cowan et al. |
| 2008/0033497 A1 | 2/2008 | Bulkes et al. |
| 2008/0039904 A1 | 2/2008 | Bulkes et al. |
| 2008/0051854 A1 | 2/2008 | Bulkes et al. |
| 2008/0058886 A1 | 3/2008 | Williams |
| 2008/0077184 A1 | 3/2008 | Denker et al. |
| 2008/0077188 A1 | 3/2008 | Denker et al. |
| 2008/0097529 A1 | 4/2008 | Parramon et al. |
| 2008/0109054 A1 | 5/2008 | Hastings et al. |
| 2008/0119911 A1 | 5/2008 | Rosero |
| 2008/0132961 A1 | 6/2008 | Jaax et al. |
| 2008/0140154 A1 | 6/2008 | Loeb et al. |
| 2008/0255628 A1 | 10/2008 | Seim |
| 2008/0288039 A1 | 11/2008 | Reddy |
| 2008/0294208 A1 | 11/2008 | Willis et al. |
| 2008/0294210 A1 | 11/2008 | Rosero |
| 2008/0319502 A1 | 12/2008 | Sunagawa et al. |
| 2009/0024180 A1 | 1/2009 | Kisker et al. |
| 2009/0048583 A1 | 2/2009 | Williams et al. |
| 2009/0082827 A1 | 3/2009 | Kveen et al. |
| 2009/0082828 A1 | 3/2009 | Ostroff |
| 2009/0171408 A1 | 7/2009 | Solem |
| 2009/0192570 A1 | 7/2009 | Jaax et al. |
| 2009/0198293 A1 | 8/2009 | Cauller et al. |
| 2009/0198295 A1 | 8/2009 | Dennis et al. |
| 2009/0198308 A1 | 8/2009 | Gross et al. |
| 2009/0281587 A1 | 11/2009 | Pei |
| 2009/0299426 A1 | 12/2009 | Kim et al. |
| 2009/0326601 A1 | 12/2009 | Brisken et al. |
| 2010/0094367 A1 | 4/2010 | Sen |

(56) References Cited

U.S. PATENT DOCUMENTS

| | | |
|---|---|---|
| 2010/0161002 A1 | 6/2010 | Aghassian et al. |
| 2010/0179628 A1 | 7/2010 | Towe et al. |
| 2010/0249883 A1 | 9/2010 | Zdeblick |
| 2010/0249885 A1 | 9/2010 | Colvin et al. |
| 2010/0286744 A1 | 11/2010 | Echt et al. |
| 2010/0304209 A1 | 12/2010 | Lund et al. |
| 2010/0305627 A1 | 12/2010 | Anderson |
| 2010/0305628 A1 | 12/2010 | Lund et al. |
| 2010/0305629 A1 | 12/2010 | Lund et al. |
| 2010/0312320 A1 | 12/2010 | Faltys et al. |
| 2011/0054555 A1 | 3/2011 | Williams et al. |
| 2011/0060392 A1 | 3/2011 | Zdeblick et al. |
| 2011/0071585 A1 | 3/2011 | Ransbury et al. |
| 2011/0071586 A1 | 3/2011 | Jacobson |
| 2011/0077708 A1 | 3/2011 | Ostroff |
| 2011/0077721 A1 | 3/2011 | Whitehurst et al. |
| 2011/0137378 A1 | 6/2011 | Klosterman et al. |
| 2011/0160801 A1 | 6/2011 | Markowitz et al. |
| 2011/0208260 A1 | 8/2011 | Jacobson |
| 2011/0245782 A1 | 10/2011 | Berthiaume et al. |
| 2011/0270339 A1 | 11/2011 | Murray, III et al. |
| 2011/0270340 A1 | 11/2011 | Pellegrini et al. |
| 2011/0282423 A1 | 11/2011 | Jacobson |
| 2011/0301656 A1 | 12/2011 | Casavant et al. |
| 2011/0313490 A1 | 12/2011 | Parramon et al. |
| 2012/0059431 A1 | 3/2012 | Williams et al. |
| 2012/0081201 A1 | 4/2012 | Norgaard et al. |
| 2012/0095521 A1 | 4/2012 | Hintz |
| 2012/0095539 A1 | 4/2012 | Khairkhahan et al. |
| 2012/0109149 A1 | 5/2012 | Bonner et al. |
| 2012/0109236 A1 | 5/2012 | Jacobson et al. |
| 2012/0116489 A1 | 5/2012 | Khairkhahan et al. |
| 2012/0143271 A1 | 6/2012 | Root et al. |
| 2012/0158090 A1 | 6/2012 | Chavan et al. |
| 2012/0158111 A1 | 6/2012 | Khairkhahan et al. |
| 2012/0165827 A1 | 6/2012 | Khairkhahan et al. |
| 2012/0172690 A1 | 7/2012 | Anderson et al. |
| 2012/0172891 A1 | 7/2012 | Lee |
| 2012/0172892 A1 | 7/2012 | Grubac et al. |
| 2012/0179219 A1 | 7/2012 | Kisker et al. |
| 2012/0197352 A1 | 8/2012 | Carbunaru et al. |
| 2012/0197373 A1 | 8/2012 | Khairkhahan et al. |
| 2012/0232371 A1 | 9/2012 | Mech et al. |
| 2012/0290021 A1 | 11/2012 | Saurkar et al. |
| 2012/0290025 A1 | 11/2012 | Keimel |
| 2012/0316622 A1 | 12/2012 | Whitehurst et al. |
| 2012/0323099 A1 | 12/2012 | Mothilal et al. |
| 2013/0023975 A1 | 1/2013 | Locsin |
| 2013/0030483 A1 | 1/2013 | Demmer et al. |
| 2013/0035748 A1 | 2/2013 | Bonner et al. |
| 2013/0066169 A1 | 3/2013 | Rys et al. |
| 2013/0073004 A1 | 3/2013 | Root et al. |
| 2013/0079798 A1 | 3/2013 | Tran et al. |
| 2013/0079861 A1 | 3/2013 | Reinert et al. |
| 2013/0103047 A1 | 4/2013 | Steingisser et al. |
| 2013/0103109 A1 | 4/2013 | Jacobson |
| 2013/0110127 A1 | 5/2013 | Bornzin et al. |
| 2013/0110219 A1 | 5/2013 | Bornzin et al. |
| 2013/0116529 A1 | 5/2013 | Min et al. |
| 2013/0116738 A1 | 5/2013 | Samade et al. |
| 2013/0116740 A1 | 5/2013 | Bornzin et al. |
| 2013/0123872 A1 | 5/2013 | Bornzin et al. |
| 2013/0123875 A1 | 5/2013 | Varady et al. |
| 2013/0131159 A1 | 5/2013 | Ko et al. |
| 2013/0131693 A1 | 5/2013 | Berthiaume et al. |
| 2013/0138004 A1 | 5/2013 | Dong et al. |
| 2013/0138006 A1 | 5/2013 | Bornzin et al. |
| 2013/0150695 A1 | 6/2013 | Biela et al. |
| 2013/0184790 A1 | 7/2013 | Schleicher et al. |
| 2013/0226259 A1 | 8/2013 | Penner et al. |
| 2013/0231710 A1 | 9/2013 | Jacobson |
| 2013/0234692 A1 | 9/2013 | Liang et al. |
| 2013/0235663 A1 | 9/2013 | Walsh et al. |
| 2013/0235672 A1 | 9/2013 | Walsh et al. |
| 2013/0238044 A1 | 9/2013 | Penner |
| 2013/0238056 A1 | 9/2013 | Poore et al. |
| 2013/0238072 A1 | 9/2013 | Deterre et al. |
| 2013/0238073 A1 | 9/2013 | Makdissi et al. |
| 2013/0238840 A1 | 9/2013 | Walsh et al. |
| 2013/0253309 A1 | 9/2013 | Allan et al. |
| 2013/0253344 A1 | 9/2013 | Griswold et al. |
| 2013/0253345 A1 | 9/2013 | Griswold et al. |
| 2013/0253346 A1 | 9/2013 | Griswold et al. |
| 2013/0253347 A1 | 9/2013 | Griswold et al. |
| 2013/0261497 A1 | 10/2013 | Pertijs et al. |
| 2013/0268042 A1 | 10/2013 | Hastings et al. |
| 2013/0274828 A1 | 10/2013 | Willis |
| 2013/0274847 A1 | 10/2013 | Ostroff |
| 2013/0282070 A1 | 10/2013 | Cowan et al. |
| 2013/0282073 A1 | 10/2013 | Cowan et al. |
| 2013/0289428 A1 | 10/2013 | Patel et al. |
| 2013/0302665 A1 | 11/2013 | Zhao et al. |
| 2013/0303872 A1 | 11/2013 | Taff et al. |
| 2013/0324825 A1 | 12/2013 | Ostroff et al. |
| 2013/0325081 A1 | 12/2013 | Karst et al. |
| 2013/0345770 A1 | 12/2013 | Dianaty et al. |
| 2014/0012342 A1 | 1/2014 | Penner et al. |
| 2014/0012344 A1 | 1/2014 | Hastings et al. |
| 2014/0018876 A1 | 1/2014 | Ostroff |
| 2014/0018877 A1 | 1/2014 | Demmer et al. |
| 2014/0026016 A1 | 1/2014 | Nicholes |
| 2014/0031836 A1 | 1/2014 | Ollivier |
| 2014/0031837 A1 | 1/2014 | Perryman et al. |
| 2014/0039570 A1 | 2/2014 | Carroll et al. |
| 2014/0039578 A1 | 2/2014 | Whitehurst et al. |
| 2014/0039588 A1 | 2/2014 | Ok et al. |
| 2014/0039591 A1 | 2/2014 | Drasler et al. |
| 2014/0046395 A1 | 2/2014 | Regnier et al. |
| 2014/0058240 A1 | 2/2014 | Mothilal et al. |
| 2014/0072872 A1 | 3/2014 | Hodgkinson et al. |
| 2014/0100627 A1 | 4/2014 | Min |
| 2014/0121720 A1 | 5/2014 | Bonner et al. |
| 2015/0238768 A1* | 8/2015 | Bornzin ............ A61N 1/37205 607/28 |

FOREIGN PATENT DOCUMENTS

| | | |
|---|---|---|
| EP | 0709114 A2 | 5/1996 |
| EP | 1541191 A1 | 6/2005 |
| EP | 1 731 195 A1 | 12/2006 |
| EP | 1549393 B1 | 2/2008 |
| TW | 1251986 B | 3/2006 |
| TW | 1252007 B | 3/2006 |
| WO | 2006099425 A1 | 9/2006 |
| WO | 2009006531 A1 | 1/2009 |
| WO | 2009052480 A2 | 4/2009 |
| WO | 2012150000 | 11/2012 |
| WO | 2012154599 A2 | 11/2012 |
| WO | 2013080038 A2 | 6/2013 |
| WO | 2014046662 | 3/2014 |
| WO | 2014/178035 A1 | 11/2014 |

OTHER PUBLICATIONS (PCT/US2015/058743) PCT Notification of Transmittal of the International Search Report and the Written Opinion of the International Searching Authority, mailed Mar. 8, 2016, 11 pages.

Demmer, et al., "Mode Switching by a Ventricular Leadless Pacing Device", U.S. Appl. No. 14/538,486, filed Nov. 11, 2014, 75 pages.

Sheldon et al., "Mode Switching by a Ventricular Leadless Pacing Device", U.S. Appl. No. 14/538,518, filed Nov. 11, 2014, 73 pages.

U.S. Appl. No. 14/538,486 by Demmer et al., filed Nov. 11, 2014.

U.S. Appl. No. 14/538,518 by Demmer et al., filed Nov. 11, 2014.

(PCT/US2015/058739) PCT Notification of Transmittal of the International Search Report and the Written Opinion of the International Searching Authority, mailed Jan. 20, 2016, 11 pages.

(PCT/US2015/058745) PCT Notification of Transmittal of the International Search Report and the Written Opinion of the International Searching Authority, mailed Feb. 3, 2016, 11 pages.

* cited by examiner

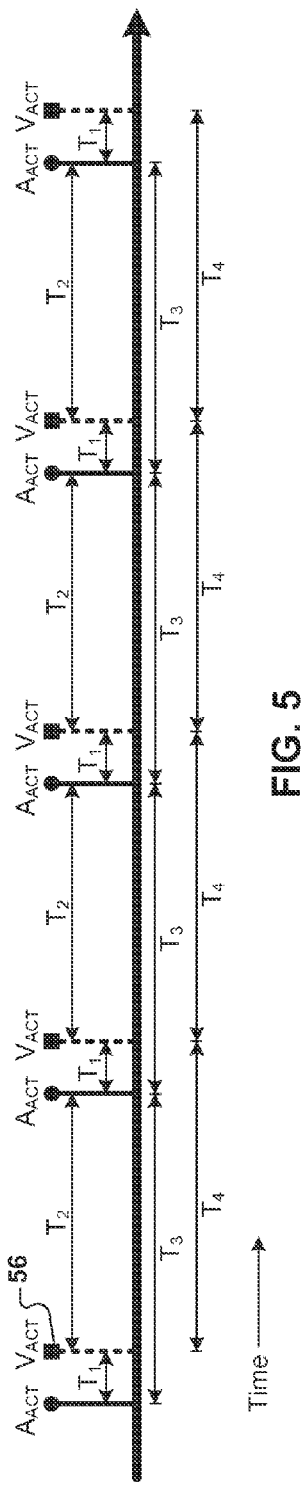

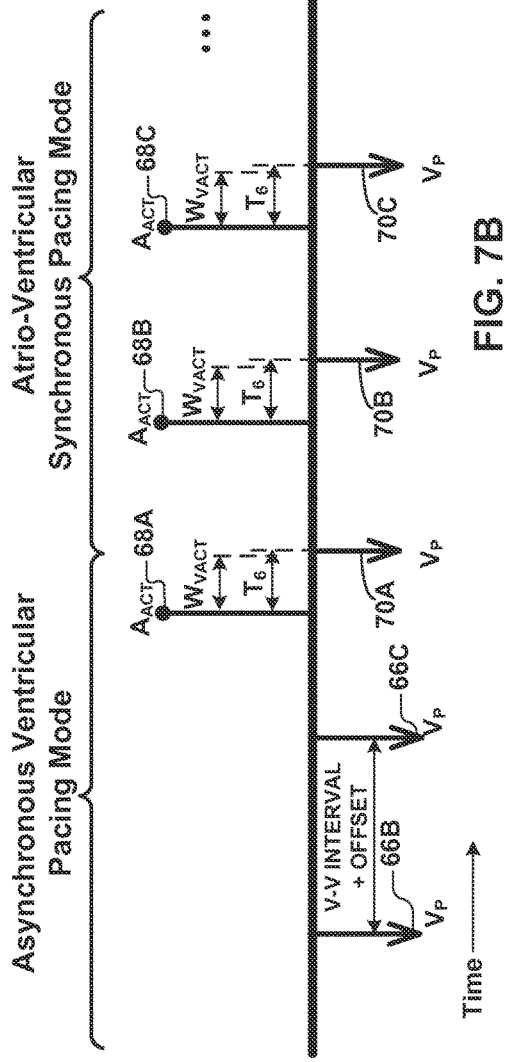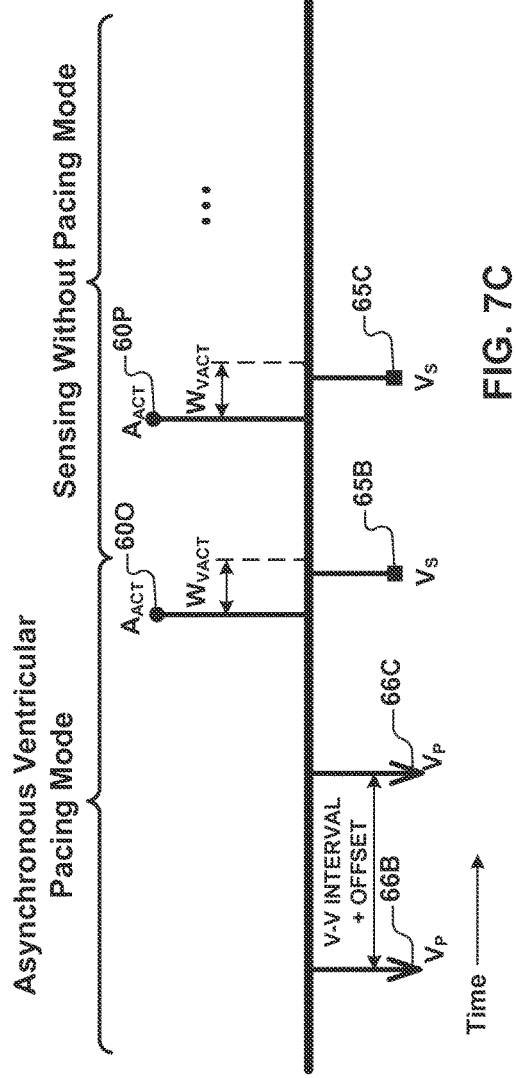

VENTRICULAR LEADLESS PACING DEVICE MODE SWITCHING

This application is a continuation in part of co-pending U.S. application Ser. No. 14/538,486, titled "MODE SWITCHING BY A VENTRICULAR LEADLESS PACING DEVICE", filed on Nov. 11, 2014, and co-pending U.S. application Ser. No. 14/538,518, titled "MODE SWITCHING BY A VENTRICULAR LEADLESS PACING DEVICE", filed on Nov. 11, 2014, both disclosures of which are herein incorporated by reference in their entirety.

TECHNICAL FIELD

The disclosure relates to cardiac pacing, and more particularly, to cardiac pacing using a leadless pacing device.

BACKGROUND

An implantable pacemaker may deliver pacing pulses to a patient's heart and monitor conditions of the patient's heart. In some examples, the implantable pacemaker comprises a pulse generator and one or more electrical leads. The pulse generator may, for example, be implanted in a small pocket in the patient's chest. The electrical leads may be coupled to the pulse generator, which may contain circuitry that generates pacing pulses and/or senses cardiac electrical activity. The electrical leads may extend from the pulse generator to a target site (e.g., an atrium and/or a ventricle) such that electrodes at the distal ends of the electrical leads are positioned at a target site. The pulse generator may provide electrical stimulation to the target site and/or monitor cardiac electrical activity at the target site via the electrodes.

A leadless pacing device has also been proposed for sensing electrical activity and/or delivering therapeutic electrical signals to the heart. The leadless pacing device may include one or more electrodes on its outer housing to deliver therapeutic electrical signals and/or sense intrinsic depolarizations of the heart. The leadless pacing device may be positioned within or outside of the heart and, in some examples, may be anchored to a wall of the heart via a fixation mechanism.

SUMMARY

The disclosure describes a leadless pacing device (hereinafter, "LPD") that is configured for implantation in a ventricle of a heart of a patient, and is configured to switch from a sensing without pacing mode to a ventricular pacing mode in response to determining that no intrinsic ventricular activity was detected within a ventricular event detection window for one or more cardiac cycles. The determination that no intrinsic ventricular activity was detected within a ventricular event detection window for one or more cardiac cycles may be referred to as loss of conduction. A processing module selects the particular ventricular pacing mode with which the LPD delivers ventricular pacing to the patient based on whether atrial oversensing is detected in combination with the loss of conduction.

In some examples, a processing module is configured to switch the LPD from the sensing without pacing mode to an atrio-ventricular synchronous pacing mode in response to determining that no intrinsic ventricular activity was detected within the ventricular event detection window for a threshold number of cardiac cycles and in response to determining that atrial oversensing is not detected. In an atrio-ventricular synchronous pacing mode, the LPD times the delivery of a pacing pulse to a ventricle of a heart of a patient relative to an atrial activation event, which may be an event that leads to a contraction of an atrium. In addition, in some examples, the processing module is configured to switch the LPD from the sensing without pacing mode to an asynchronous ventricular pacing mode in response to detecting both atrial oversensing and determining that no intrinsic ventricular activity was detected within the ventricular event detection window for a threshold number of cardiac cycles. In an asynchronous ventricular pacing mode, the LPD is configured to time the delivery of a ventricular pacing pulse relative to a previous ventricular activation event, which can be an intrinsic ventricular depolarization or delivery of a ventricular pacing pulse.

In one aspect, the disclosure is directed to a method comprising detecting, by a processing module of a leadless pacing device, atrial oversensing while the leadless pacing device is in a sensing without pacing mode; determining, by the processing module and based on an electrical cardiac signal, whether intrinsic ventricular activity is occurring in conjunction with the atrial oversensing; in response to determining intrinsic ventricular activity is occurring in conjunction with the atrial oversensing, controlling, by the processing module, the leadless pacing device to continue operating in the sensing without pacing mode; and in response to determining intrinsic ventricular activity is not occurring in conjunction with the atrial oversensing, controlling, by the processing module, the leadless pacing device to deliver a ventricular pacing pulse to the patient according to an asynchronous ventricular pacing mode.

In another aspect, the disclosure is directed to a leadless pacing system comprising a leadless pacing device configured to sense an electric cardiac signal and configured to operate in a sensing without pacing mode and an asynchronous ventricular pacing mode, and a processing module configured to detect atrial oversensing while the leadless pacing device is in a sensing without pacing mode, determine, based on the electrical cardiac signal, whether intrinsic ventricular activity is occurring in conjunction with the atrial oversensing, in response to determining intrinsic ventricular activity is occurring in conjunction with the atrial oversensing, control the leadless pacing device to continue operating in the sensing without pacing mode, and in response to determining intrinsic ventricular activity is not occurring in conjunction with the atrial oversensing, control the leadless pacing device to deliver a ventricular pacing pulse to the patient according to an asynchronous ventricular pacing mode.

In another aspect, disclosure is directed to a system comprising means for detecting atrial oversensing while a leadless pacing device is in a sensing without pacing mode; means for determining, based on an electrical cardiac signal, whether intrinsic ventricular activity is occurring in conjunction with the atrial oversensing; means for controlling the leadless pacing device to continue operating in the sensing without pacing mode in response to determining intrinsic ventricular activity is occurring in conjunction with the atrial oversensing; and means for controlling the leadless pacing device to deliver a ventricular pacing pulse to the patient according to an asynchronous ventricular pacing mode in response to determining intrinsic ventricular activity is not occurring in conjunction with the atrial oversensing.

In another aspect, the disclosure is directed to a computer-readable storage medium comprising instructions that, when executed by a processing module, cause the processing module to detect atrial oversensing while a leadless pacing device is in a sensing without pacing mode; determine, based on an electrical cardiac signal, whether intrinsic ventricular activity is occurring in conjunction with the atrial oversensing; in response to determining intrinsic ventricular activity is occurring in conjunction with the atrial oversensing, control the leadless pacing device to continue operating in the sensing without pacing mode; and in response to determining intrinsic ventricular activity is not occurring in conjunction with the atrial oversensing, control the leadless pacing device to deliver a ventricular pacing pulse to the patient according to an asynchronous ventricular pacing mode.

In another aspect, the disclosure is directed to a method comprising detecting, by a processing module and based on an electrical cardiac signal sensed by a leadless pacing device while the leadless pacing device is in a sensing without pacing mode, loss of conduction of a heart of a patient; determining, by the processing module, whether atrial oversensing is occurring in conjunction with the loss of conduction; in response to determining the atrial oversensing is not occurring in conjunction with the loss of conduction, controlling, by the processing module, the leadless pacing device to deliver ventricular pacing pulses to the patient according to an atrio-ventricular synchronous pacing mode; and in response to determining the atrial oversensing is occurring in conjunction with the loss of conduction, controlling, by the processing module, the leadless pacing device to deliver ventricular pacing pulses to the patient according to an asynchronous ventricular pacing mode.

In another aspect, the disclosure is directed to a system comprising a leadless pacing device configured to sense an electric cardiac signal and configured to operate in a sensing without pacing mode, an atrio-ventricular pacing mode, and an asynchronous ventricular pacing mode, and a processing module configured to detect loss of conduction of a heart of a patient based on the electrical cardiac signal, determine whether atrial oversensing is occurring in conjunction with the loss of conduction, in response to determining the atrial oversensing is not occurring in conjunction with the loss of conduction, control the leadless pacing device to deliver ventricular pacing pulses to the patient according to an atrio-ventricular synchronous pacing mode, and in response to determining the atrial oversensing is occurring in conjunction with the loss of conduction, control the leadless pacing device to deliver ventricular pacing pulses to the patient according to an asynchronous ventricular pacing mode.

In another aspect, the disclosure is directed to a system comprising means for detecting, based on an electrical cardiac signal sensed by a leadless pacing device while the leadless pacing device is in a sensing without pacing mode, loss of conduction of a heart of a patient; means for determining whether atrial oversensing is occurring in conjunction with the loss of conduction; means for the leadless pacing device to deliver ventricular pacing pulses to the patient according to an atrio-ventricular synchronous pacing mode in response to determining the atrial oversensing is not occurring in conjunction with the loss of conduction; and means for controlling the leadless pacing device to deliver ventricular pacing pulses to the patient according to an asynchronous ventricular pacing mode in response to determining the atrial oversensing is occurring in conjunction with the loss of conduction, controlling.

In another aspect, the disclosure is directed to a computer-readable storage medium comprising instructions that, when executed by a processing module, cause the processing module to detect, based on an electrical cardiac signal sensed by a leadless pacing device while the leadless pacing device is in a sensing without pacing mode, loss of conduction of a heart of a patient; determine whether atrial oversensing is occurring in conjunction with the loss of conduction; in response to determining the atrial oversensing is not occurring in conjunction with the loss of conduction, control the leadless pacing device to deliver ventricular pacing pulses to the patient according to an atrio-ventricular synchronous pacing mode; and in response to determining the atrial oversensing is occurring in conjunction with the loss of conduction, control the leadless pacing device to deliver ventricular pacing pulses to the patient according to an asynchronous ventricular pacing mode.

In another aspect, the disclosure is directed to a computer-readable storage medium comprising computer-readable instructions for execution by a processor. The instructions cause a programmable processor to perform any whole or part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, read only memory (ROM), or random access memory (RAM)) or any other type of volatile or non-volatile memory that stores instructions (e.g., in the form of a computer program or other executable) to cause a programmable processor to perform the techniques described herein. In some examples, the computer-readable medium is an article of manufacture and is non-transitory.

The details of one or more examples are set forth in the accompanying drawings and the description below. Other features, objects, and advantages will be apparent from the description and drawings, and from the claims.

BRIEF DESCRIPTION OF THE DRAWINGS

FIG. 5 is a timing diagram illustrating normal conduction timing in a patient.

FIG. 6A is a timing diagram illustrating an example technique for controlling a leadless pacing device to switch from a sensing without pacing mode to an atrio-ventricular synchronous pacing mode.

FIG. 7B is a timing diagram illustrating an example technique for controlling a leadless pacing device to switch from an asynchronous ventricular pacing mode to an atrio-ventricular synchronous pacing mode.

FIG. 7C is a timing diagram illustrating an example technique for controlling a leadless pacing device to switch from an asynchronous ventricular pacing mode to a sensing without pacing mode.

DETAILED DESCRIPTION

Figure 1:
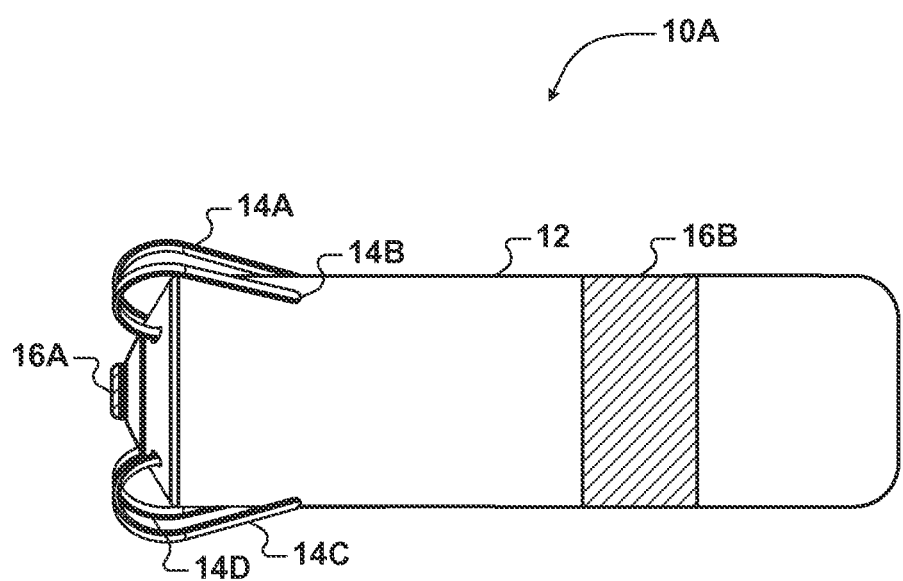
FIG. 1 is a conceptual diagram illustrating an example leadless pacing device configured to operate in a sensing without pacing mode and to deliver atrio-ventricular synchronous pacing and asynchronous ventricular pacing.

In some cases, a dual-chamber implantable pacemaker is implanted within a pocket within a patient's chest, and coupled to a right-atrial lead and a right-ventricular lead. The right-atrial lead extends from the implantable pacemaker to the right atrium of the patient's heart, and positions one or more electrodes within the right atrium. The right-ventricular lead extends from the implantable pacemaker to the right ventricle of the patient's heart, and positions one or more electrodes within the right ventricle. Such dual-chamber implantable pacemakers sense respective cardiac electrical activity, e.g., respective cardiac electrograms, via the one or more electrodes implanted within the right atrium and the one or more electrodes implanted within the right ventricle. In particular, such dual-chamber implantable pacemakers detect intrinsic atrial depolarizations via the one or more electrodes implanted within the right atrium, and intrinsic ventricular depolarizations via the one or more electrodes implanted within the right ventricle. The implantable pacemakers may also deliver pacing pulses to the right atrium and the right ventricle via the one or more electrodes in the right atrium and the right ventricle, respectively.

Due to the ability to sense both atrial and ventricular electrical activity, dual-chamber implantable pacemakers may be able to provide atrio-ventricular synchronous pacing. For patients with intermittent AV node conduction, it may be desirable to inhibit ventricular pacing and allow an intrinsic ventricular depolarization to occur for a time, referred to as the A-V interval, after an intrinsic atrial depolarization or atrial pace. Such atrio-ventricular synchronous pacing by dual-chamber implantable pacemakers may be according to the VDD or DDD programming modes, which have been used to treat patients with various degrees of AV block.

Alternatively, dual-chamber implantable pacemakers may provide asynchronous ventricular pacing. Asynchronous ventricular pacing may be desirable if the patient's heart rate becomes irregular. According to an asynchronous ventricular pacing mode, the dual-chamber implantable pacemaker delivers a ventricular pacing pulse if an intrinsic ventricular depolarization is not detected within a "V-V interval" that begins when a previous intrinsic depolarization was detected, or a previous ventricular pacing pulse was delivered. Such asynchronous ventricular pacing by dual-chamber implantable pacemakers is referred to as the V-VI programming mode, or V-VIR programming mode if the V-V interval is rate-adaptive (i.e., the implantable pacemaker can sense changes in the patient's heart rate or the physiological demand for a greater or lesser heart rate, and alter the V-V interval accordingly).

Implantable cardiac leads and the pocket in which pacemakers are implanted may be associated with complications. To avoid such complications, leadless pacing devices sized to be implanted entirely within the heart, e.g., in one chamber, such as the right ventricle, of the heart have been proposed. Some proposed leadless pacing devices include a plurality of electrodes that are affixed to, or are a portion of, the housing of the respective leadless pacing device ("LPD").

An LPD described herein is configured to operate in a sensing without pacing mode (e.g., a mode corresponding to the ODO mode of a dual chamber pacemaker with leads). For example, the LPD may operate in the sensing without pacing mode as an initial mode upon implantation of the LPD in a ventricle, prior to delivering any pacing therapy to the patient. In the sensing without pacing mode, the LPD senses electrical cardiac activity, but does not deliver any pacing therapy to the heart of the patient. In addition, the LPD described herein is configured to pace in an atrio-ventricular synchronous pacing mode and an asynchronous ventricular pacing mode. In the asynchronous ventricular pacing mode, the LPD may deliver ventricular pacing pulses that are asynchronous to atrial activity. In addition, in some examples, the asynchronous pacing may, in some examples, be inhibited ventricular pacing that is not synchronized to atrial events.

As discussed below, a processing module may be configured to control the LPD to switch from the sensing without pacing mode to ventricular pacing mode in response to determining that no intrinsic ventricular activity was detected within a ventricular event detection window. The determination that no intrinsic ventricular activity was detected within the ventricular event detection window may indicate that the heart of the patient is not conducting normally, e.g., due to A-V block, such that ventricular pacing may be desirable to help maintain cardiac function of the patient at a physiologically sufficient level. Thus, the determination that no intrinsic ventricular activity may be referred to as the detection of a loss of conduction.

The processing module may select the particular ventricular pacing mode based on whether the ventricular sensing is occurring in conjunction with atrial oversensing (e.g., atrial oversensing was also detected in the same one or more cardiac cycles or the same time frame in which no intrinsic ventricular activity was detected within a ventricular event detection window). In some examples, the processing module selects the atrio-ventricular synchronous pacing mode in response to detecting, while the LPD is in the sensing without pacing mode, no intrinsic ventricular activity was detected within a ventricular event detection window for at least one cardiac cycle, and in response to determining atrial oversensing is not occurring. In addition, in some examples, the processing module selects the asynchronous ventricular pacing mode in response to detecting, while the LPD is the sensing without pacing mode, atrial oversensing and determining that no intrinsic ventricular activity was detected within a ventricular event detection window for at least one cardiac cycle. When the LPD switches to the atrio-ventricular synchronous pacing mode or the asynchronous ventricular pacing mode, the LPD begins delivering pacing stimulation to a ventricle of a heart of the patient.

Due to the placement of the LPD within a ventricle, the electrical activity of the right atrium sensed by the electrodes of the LPD implanted in the ventricle may be relatively low power (e.g., a low amplitude P-wave). Thus, the LPD may be programmed with a relatively sensitive setting for detecting atrial events. The sensitive setting may include, for example, a relatively wide bipole, a relatively low amplitude threshold, or any combination thereof. The relatively sensitive atrial event detection setting, however, may result in a processing module of the LPD characterizing electrical noise, such as noise from electromagnetic interference (EMI), as an atrial activation event. This may result in an atrial oversensing event, in which the processing module senses multiple atrial activation events within a single cardiac cycle. In some examples, the processing module detects atrial oversensing that results in a switch to the asynchronous ventricular pacing mode in response to detecting a threshold number of atrial oversensing events.

The LPD may determine that no intrinsic ventricular activity was detected when the LPD does not detect (e.g., sense), for a predetermined number of cardiac cycles, a ventricular sense event at an expected time, which may be within a ventricular event detection window $W_{VACT}$ that begins at a prior ventricular sense event, a prior ventricular pacing event, or a prior atrial sense or pacing event. A ventricular sense event may also be referred to as a ventricular depolarization event. Each determination by the LPD that no intrinsic ventricular activity was detected within the ventricular event detection window may indicate that the ventricle did not intrinsically conduct at the expected time following the atrial activation event. The ventricle may not intrinsically conduct due to, for example, AV block. Thus, the loss of conduction may occur due to AV block.

The ventricular event detection window used to detect intrinsic ventricular activation events that indicate intrinsic ventricular inactivity is not occurring and, therefore, a switch to a ventricular pacing mode may not be necessary, may begin relative to different events, depending on whether atrial oversensing is occurring. For example, if atrial oversensing is not occurring, a processing module of the LPD or another device may use the time at which an atrial activation event is detected to determine whether an intrinsic ventricular activation event is detected. For example, the ventricular event detection window may begin at the atrial activation event. If atrial oversensing is occurring, however, then the processing module may use the time at which an intrinsic ventricular activation event occurred in a prior cardiac cycle or the time at which the intrinsic ventricular activation event is expected to occur, e.g., based on a heart rate of the patient or based on a stored frequency of intrinsic ventricular activation events, to determine whether an intrinsic ventricular activation event is detected. For example, the ventricular event detection window may begin at the intrinsic ventricular activation event of a prior cardiac cycle or at the time at which an intrinsic ventricular activation event is expected to occur.

In some examples, a processing module determines that intrinsic ventricular activity is not occurring in response to detecting a threshold number of cardiac cycles in which a ventricular sense event is not detected within a ventricular event detection window. The processing module can count the number of cardiac cycles in which a ventricular sense event is not detected using a loss of conduction counter, which may track the number of successive cardiac cycles in which a ventricular sense event is not detected. In some examples, the loss of conduction counter may be an "X of Y" type counter, in which the counter tracks the number of cardiac cycles ("X") out of a particular number of consecutive cardiac cycles ("Y"), in which a ventricular sense event is not detected. "X" can be one, two, three, four or more, and "Y," which is greater than or equal to "X" can be, for example, three, four, five, six or more in some examples. A cardiac cycle in which a ventricular sense event is not detected may be referred to as a loss of conduction event.

In examples in which the threshold number of loss of conduction events is more than one, the ventricle of the heart of the patient may not properly depolarize or contract in the cardiac cycle in which the intrinsic ventricular activation event was not detected. As a result, the heart of the patient may skip a beat. This may be referred to as a "dropping" of a heart beat by the LPD. By being configured to drop one or more heart beats, the LPD may be configured to favor the intrinsic conduction of the heart by providing time for the heart to resume intrinsic conduction or for LPD to sense the intrinsic conduction before the LPD switches to an atrio-ventricular synchronous pacing mode or an asynchronous ventricular pacing mode, in which the LPD delivers a ventricular pacing pulse that may override the intrinsic conduction of the heart. In this way, the LPD may sense the intrinsic activity of the heart for at least one full beat before delivering a ventricular pacing pulse.

The threshold number of loss of conduction events affects the number of beats that may be dropped before the LPD switches to a ventricular pacing mode. For example, if the threshold number of loss of conduction events is one, then the heart may drop one beat before the LPD switches to either the atrio-ventricular synchronous pacing mode or the asynchronous ventricular pacing mode. As another example, if the threshold value is two, then the heart may drop two beats before the LPD switches to the atrio-ventricular synchronous pacing mode or the asynchronous ventricular pacing mode.

In some examples, the atrio-ventricular synchronous pacing mode is ventricular inhibited. Thus, in some examples, when LPD is in the atrio-ventricular synchronous pacing mode, LPD may deliver a ventricular pacing pulse if a ventricular sense event is not detected within a particular detection window of an atrial activation event.

If atrial oversensing occurs in combination with determination that no intrinsic ventricular activity was detected within a ventricular event detection window for at least one cardiac cycle, the processing module may be unable to time the delivery of the ventricular pacing pulse in the atrio-ventricular synchronous pacing mode relative to an atrial activation event. For example, the processing module may not be able to discern which detected atrial activation event corresponds to actual atrial activation, rather than electrical noise. Accordingly, in examples described herein, in response to detecting atrial oversensing in combination with a determination that no intrinsic ventricular activity was detected within a ventricular event detection window for at least one cardiac cycle, the processing module implements an asynchronous ventricular pacing mode in which the processing module controls the timing of the delivery of the ventricular pacing pulse relative to a prior-detected ventricular activation event (e.g., an intrinsic ventricular depolarization or a ventricular pacing pulse). Because the heart rate of a patient may not change suddenly, a prior ventricular activation rate (e.g., a V-V interval) may be an effective ventricular pacing rate during atrial oversensing. As noted above, however, in some examples, the asynchronous pacing may be a ventricular inhibited pacing, such that the LPD may not deliver a ventricular pacing pulse if a ventricular sense event is detected within a particular detection window, e.g., which may begin at a prior ventricular sense event or a ventricular pacing event.

In some examples, if, after switching to the atrio-synchronous ventricular pacing mode, the processing module senses a threshold number of cardiac cycles in which atrial oversensing occurs, each of these cardiac cycles being referred to herein as an atrial oversensing event, within a particular number of cardiac cycles, then the processing module may switch the LPD from the atrio-ventricular synchronous pacing mode to an asynchronous ventricular pacing mode. When switched to the atrio-ventricular synchronous pacing mode to the asynchronous ventricular pacing mode, the LPD terminates delivery of pacing pulses according to the atrio-ventricular synchronous mode and delivers pacing pulses to the patient in accordance with the asynchronous ventricular pacing mode.

FIG. 1 is a conceptual diagram illustrating an example LPD 10A that is configured to operating in a sensing without pacing mode, and deliver atrio-ventricular synchronous pacing and asynchronous ventricular pacing. In some examples, whether LPD 10A is operating in a sensing without pacing mode, in an atrio-ventricular synchronous pacing mode, or in an asynchronous ventricular pacing mode is controlled based on the detection of atrial oversensing and a determination that no intrinsic ventricular activity was detected within a ventricular event detection window for at least one cardiac cycle, as described in further detail below the respect to FIGS. 6A-8.

As illustrated in FIG. 1, LPD 10A includes an outer housing 12, fixation times 14A-14D (collectively "fixation tines 14"), and electrodes 16A and 16B. Outer housing 12 is configured such that, e.g., has a size and form factor, that allows LPD 10A to be entirely implanted within a chamber of a heart, such as a right ventricle. As illustrated in FIG. 1, housing 12 may have a cylindrical (e.g., pill-shaped) form factor in some examples. Housing 12 may be hermetically sealed to prevent ingress of fluids into the interior of housing 12.

Fixation tines 14 extend from outer housing 12, and are configured to engage with cardiac tissue to substantially fix a position of housing 12 within a chamber of a heart, e.g., at or near an apex of a right ventricle. Fixation tines 14 are configured to anchor housing 12 to the cardiac tissue such that LPD 10A moves along with the cardiac tissue during cardiac contractions. Fixation tines 14 may be fabricated from any suitable material, such as a shape memory material (e.g., Nitinol). The number and configuration of fixation tines 14 illustrated in FIG. 1 is merely one example, and other numbers and configurations of fixation tines for anchoring an LPD housing to cardiac tissue are contemplated. Additionally, although LPD 10A includes a plurality of fixation tines 14 that are configured to anchor LPD 10A to cardiac tissue in a chamber of a heart, in other examples, LPD 10A may be fixed to cardiac tissue using other types of fixation mechanisms, such as, but not limited to, barbs, coils, and the like.

LPD 10A is configured to sense electrical activity of a heart, i.e., a cardiac electrogram ("EGM"), and deliver pacing pulses to a right ventricle, via electrodes 16A and 16B. Electrodes 16A and 16B may be mechanically connected to housing 12, or may be defined by a portion of housing 12 that is electrically conductive. In either case, electrodes 16A and 16B are electrically isolated from each other. Electrode 16A may be referred to as a tip electrode, and fixation tines 14 may be configured to anchor LPD 10A to cardiac tissue such that electrode 16A maintains contact with the cardiac tissue. Electrode 16B may be defined by a conductive portion of housing 12 and, in some examples, may define at least part of a power source case that houses a power source (e.g., a battery) of LPD 10A. In some examples, a portion of housing 12 may be covered by, or formed from, an insulative material to isolate electrodes 16A and 16B from each other and/or to provide a desired size and shape for one or both of electrodes 16A and 16B.

Outer housing 12 houses electronic components of LPD 10A, e.g., an electrical sensing module for sensing cardiac electrical activity via electrodes 16A and 16B, a sensor, and an electrical stimulation module for delivering pacing pulses via electrodes 16A and 16B. Electronic components may include any discrete and/or integrated electronic circuit components that implement analog and/or digital circuits capable of producing the functions attributed to an LPD described herein. Additionally, housing 12 may house a memory that includes instructions that, when executed by one or more processors housed within housing 12, cause LPD 10A to perform various functions attributed to LPD 10A herein. In some examples, housing 12 may house a communication module that enables LPD 10A to communicate with other electronic devices, such as a medical device programmer. In some examples, housing 12 may house an antenna for wireless communication. Housing 12 may also house a power source, such as a battery. The electronic components of LPD 10A are described in further detail below, with respect to FIG. 4.

Figure 2:
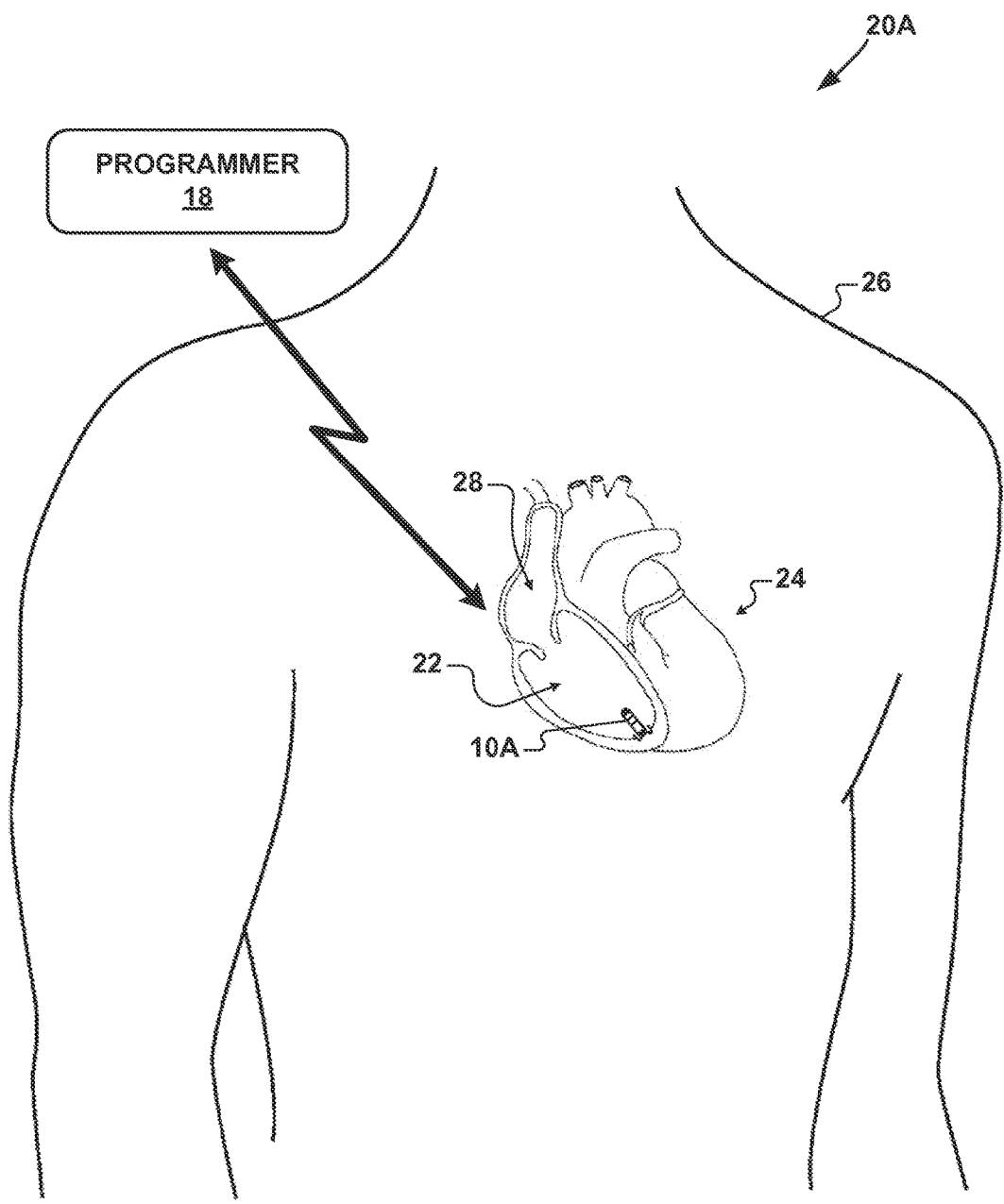
FIG. 2 is a conceptual diagram illustrating a leadless pacing system that comprises the example leadless pacing device of FIG. 1.

FIG. 2 is a conceptual diagram illustrating an example leadless pacing system 20A that comprises the example LPD 10A from FIG. 1. In the example of FIG. 2, LPD 10A is implanted within right ventricle 22 of heart 24 of patient 26. More particularly, LPD 10A is fixed or attached to the inner wall of the right ventricle 22 proximate to the apex of the right ventricle in the example of FIG. 2 via the fixation tines 14. In other examples, LPD 10A may be fixed to the inner wall of right ventricle 22 at another location, e.g., on the intraventricular septum or free-wall of right ventricle 22, or may be fixed to the outside of heart 24, e.g., epicardially, proximate to right ventricle 22. In other examples, LPD 10A may be fixed within, on, or near the left-ventricle of heart 24.

LPD 10A includes a plurality of electrodes that are affixed to, or are a portion of, the housing of LPD 10A, i.e., electrodes 16A and 16B. LPD 10A may be configured to sense electrical cardiac signals associated with depolarization and repolarization of heart 24, e.g., an EGM, via electrodes 16A and 16B. LPD 10A is also configured to deliver cardiac pacing pulses to right ventricle 22 via electrodes 16A and 16B. In some examples, LPD 10A may deliver the cardiac pacing pulses according to an atrio-ventricular synchronous pacing mode or an asynchronous ventricular pacing mode.

LPD 10A is configured to detect a ventricular activation event in any suitable way. In some examples, a processing module of LPD 10A is configured to detect a ventricular activation event based on ventricular electrical activity (e.g., an R-wave), which may be indicative of an intrinsic depolarization of right ventricle 22. In addition to, or instead of, the ventricular electrical activity, the processing module is configured to detect a ventricular activation event based on the delivery of a pacing pulse to right ventricle 22. In yet other examples, the processing module may be configured to detect a ventricular activation event based on detection of a ventricular contraction, which may be detected based on heart sounds (e.g., the Si heart sounds) sensed by a sensor of LPD 10A, or based on motion of the right ventricle (e.g., sensed by a motion sensor of LPD 10A or another device).

LPD 10A is configured to detect an atrial activation event in any suitable way. In some examples, LPD 10A is configured to detect an atrial activation event based on a mechanical contraction of right atrium 28, based on detection of an atrial depolarization within the electrical cardiac signal, or based on both the mechanical contraction and the atrial depolarization. LPD 10A may, for example, detect an atrial depolarization by at least detecting a P-wave, which represents atrial depolarization, within the electrical cardiac signal.

In some examples, LPD 10A may, at times, oversense atrial activation events. For example, due to the quality of the electrical signal sensed by electrodes 16A, 16B of LPD 10A, or the relatively small magnitude of the atrial depolarizations (e.g., small P-wave amplitude) within the sensed electrical cardiac signal, LPD 10A may be programmed with a relatively sensitive setting for detecting atrial events, which may result in the characterization of electrical noise as an atrial activation event. This may result in an atrial oversensing event, in which the processing module senses multiple electrical events that are characterized as atrial activation events within a single cardiac cycle. As described in greater detail below, in some examples, LPD 10A is configured to switch from a sensing without pacing mode to an atrio-ventricular synchronous pacing mode in response to detecting loss of conduction, e.g., determining that no intrinsic ventricular activity was detected within a ventricular event detection window for at least one cardiac cycle, and in response to determining that atrial oversensing is not detected. In addition, in some examples, LPD 10A is configured to switch from an atrio-ventricular synchronous pacing mode to an asynchronous ventricular pacing mode in response to detecting a threshold number of atrial oversensing events within a particular time period, which may be measured in any suitable manner, such as based on a number of cardiac cycles or based on a duration of time.

In contrast to LPD 10A, a dual chamber pacemaker that is electrically connected to leads that extend into right ventricle 22 and right atrium 28 of heart 24, LPD 10A (as well as other LPDs) may sense atrial activity with electrodes placed within right atrium 28. As a result, the amplitude of the P-wave of an electrical cardiac signal sensed by the dual chamber pacemaker (or other pacemaker with leads in right atrium 28) may be larger than the amplitude of the P-wave of an electrical cardiac signal sensed by LPD 10A. An electrical cardiac signal with larger P-wave amplitudes may result in fewer atrial oversensing events, e.g., due at least in part to the sensing thresholds with which LPD 10A may detect atrial activation events. Thus, a switch from a sensing without pacing mode to an atrio-ventricular synchronous pacing mode in response to detection of atrial oversensing, or from an atrio-ventricular synchronous pacing mode to an asynchronous ventricular pacing mode in response to detecting a threshold number of atrial oversensing events, as described herein with respect to LPDs, may not be applicable to a dual chamber pacemaker (or other pacemaker with leads in right atrium 28) or provide improved utility of the dual chamber pacemaker.

As illustrated in FIG. 2, LPD system 20A also includes a medical device programmer 18, which is configured to program LPD 10A and retrieve data from LPD 10A. Programmer 18 may be a handheld computing device, a desktop computing device, a networked computing device, etc. Programmer 18 may include a computer-readable storage medium having instructions that cause a processing module of programmer 18 to provide the functions attributed to programmer 18 in the present disclosure. LPD 10A may wirelessly communicate with programmer 18. For example, LPD 10A may transfer data to programmer 18 and may receive data from programmer 18. Programmer 18 may also wirelessly program and/or wirelessly charge LPD 10A.

Data retrieved from LPD 10A using programmer 18 may include electrical cardiac signals stored by LPD 10A that indicate the electrical activity of heart 24, generated loss of conduction indications, atrial oversensing indications, and marker channel data that indicates the occurrence and timing of sensing, diagnosis, and therapy events associated with LPD 10A, e.g., detection of atrial and ventricular depolarizations and delivery of pacing pulses. Data transferred to LPD 10A using programmer 18 may include, for example, operational programs for LPD 10A that cause LPD 10A to operate as described herein. As examples, data transferred to LPD 10A using programmer 18 may include lengths of any A-V intervals, lengths of any V-V intervals, ventricular activation event detection windows, atrial activation event detection windows, and offsets for determining modified ventricular or atrial activation event detection windows, which are each described in further detail below. It may also include any threshold values, such as for detecting atrial and/or ventricular contractions, for detecting an oversensing event (e.g., based on a number of oversensing indications), or programming used by LPD 10A to determine such values based on determined parameters of heart 24, patient 26, or LPD 10A.

Figure 3A:
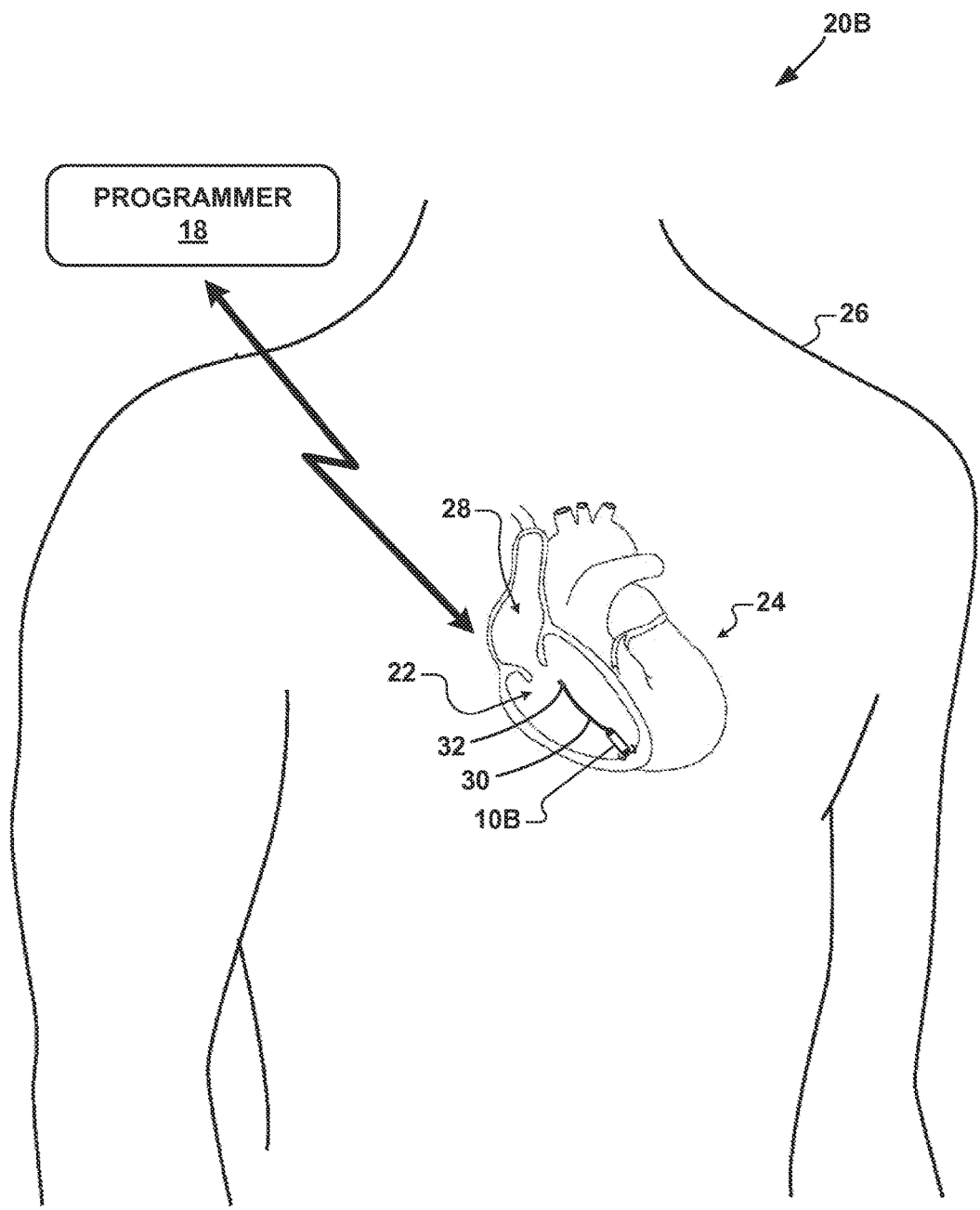
FIG. 3A is a conceptual diagram illustrating another example leadless pacing system that comprises a leadless pacing device configured to operate in a sensing without pacing mode and to deliver atrio-ventricular synchronous pacing and asynchronous ventricular pacing.
Figure 3B:
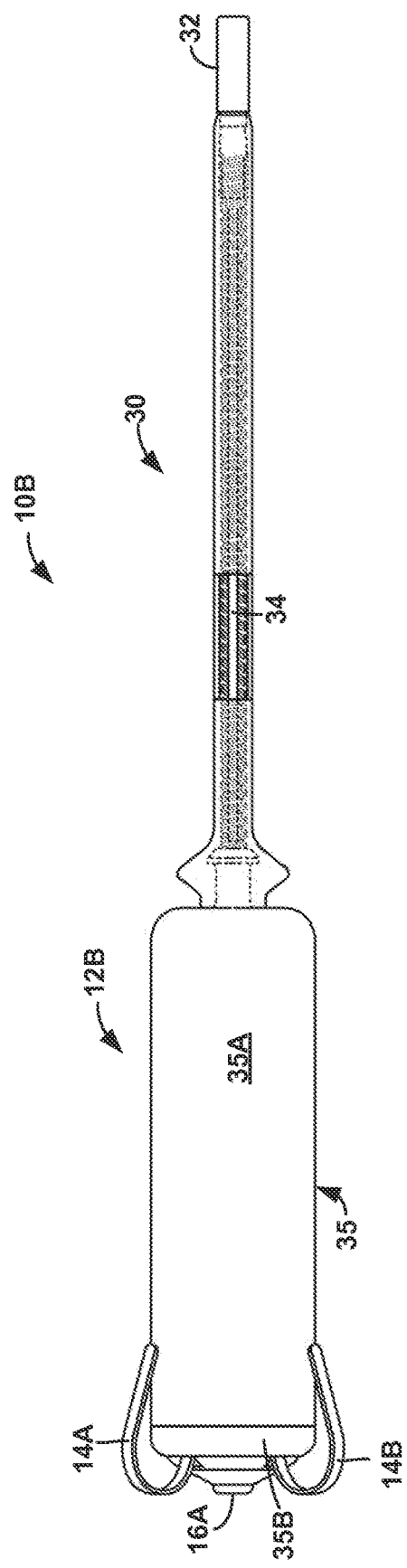
FIG. 3B is a conceptual diagram illustrating the leadless pacing device of FIG. 3A.

FIG. 3A is a conceptual diagram illustrating another example leadless pacing system 20B that comprises another example LPD 10B configured to switch from a sensing without pacing mode to an atrio-ventricular synchronous pacing mode in response to detecting atrial oversensing and determining that no intrinsic ventricular activity was detected within a ventricular event detection window for at least one cardiac cycle. FIG. 3B illustrates LPD 10B in further detail. Leadless pacing system 20B and LPD 10B may be substantially the same as leadless pacing system 20A and LPD 10A described above with respect to FIGS. 1 and 2. Unlike LPD 10A, however, LPD 10B is coupled to a sensing extension 30 that includes an electrode 32. In some examples, sensing extension 30 may include one or more additional electrodes having the same polarity as electrode 32. Although not illustrated in FIGS. 3A and 3B, LPD 10B may include an electrode 16A but may not include electrode 16B, as described above with respect to LPD 10A and FIG. 1.

Electrode 32 is electrically connected to electronics within a housing of LPD 10B (e.g., an electrical sensing module and a stimulation module) via an electrical conductor 34 of sensing extension 30. In some examples, electrical conductor 34 is connected to the electronics via an electrically conductive portion 36A of outer housing 36 of LPD 12B, which may correspond to electrode 16B of LPD 10A (FIG. 1), but may be substantially completely insulated (e.g., completely electrically insulated or nearly completely electrically insulated). Substantially completely electrically insulating conductive portion 36A of housing 36 may allow an electrical sensing module of LPD 10B to sense electrical cardiac activity with electrode 32 of sensing extension 30, rather than conductive portion 36A of housing 36. This may help improve the magnitude of the atrial depolarization present within an electrical cardiac signal sensed via LPD 10B, particularly relative to the examples in which electrodes 16A, 16B are affixed to, or are a portion of, the housing of LPD 10A (FIG. 1).

Additionally, as shown in FIGS. 3A and 3B, sensing extension 30 extends away from LPD 10B, which enables electrode 32 to be positioned relatively close to right atrium 28. As a result, an electrical cardiac signal sensed by LPD 10B via electrodes 16A (FIG. 1) and 32 may include a higher amplitude far-field atrial depolarization signal than an electrical cardiac signal sensed by LPD 10A via electrodes 16A and 16B (FIG. 1). In this way, sensing extension 30 may facilitate detection of atrial depolarizations when LPD 10B is implanted in right ventricle 22. In some examples, sensing extension 30 is sized to be entirely implanted within right ventricle 22. In other examples, sensing extension 30 is sized to extend into right atrium 28.

While the remainder of the disclosure primarily refers to LPD 10A, the techniques described with respect to LPD 10A also apply to LPD 10B, as well as other LPDs configured to provide both atrio-synchronous ventricular pacing and asynchronous ventricular pacing.

Figure 4:
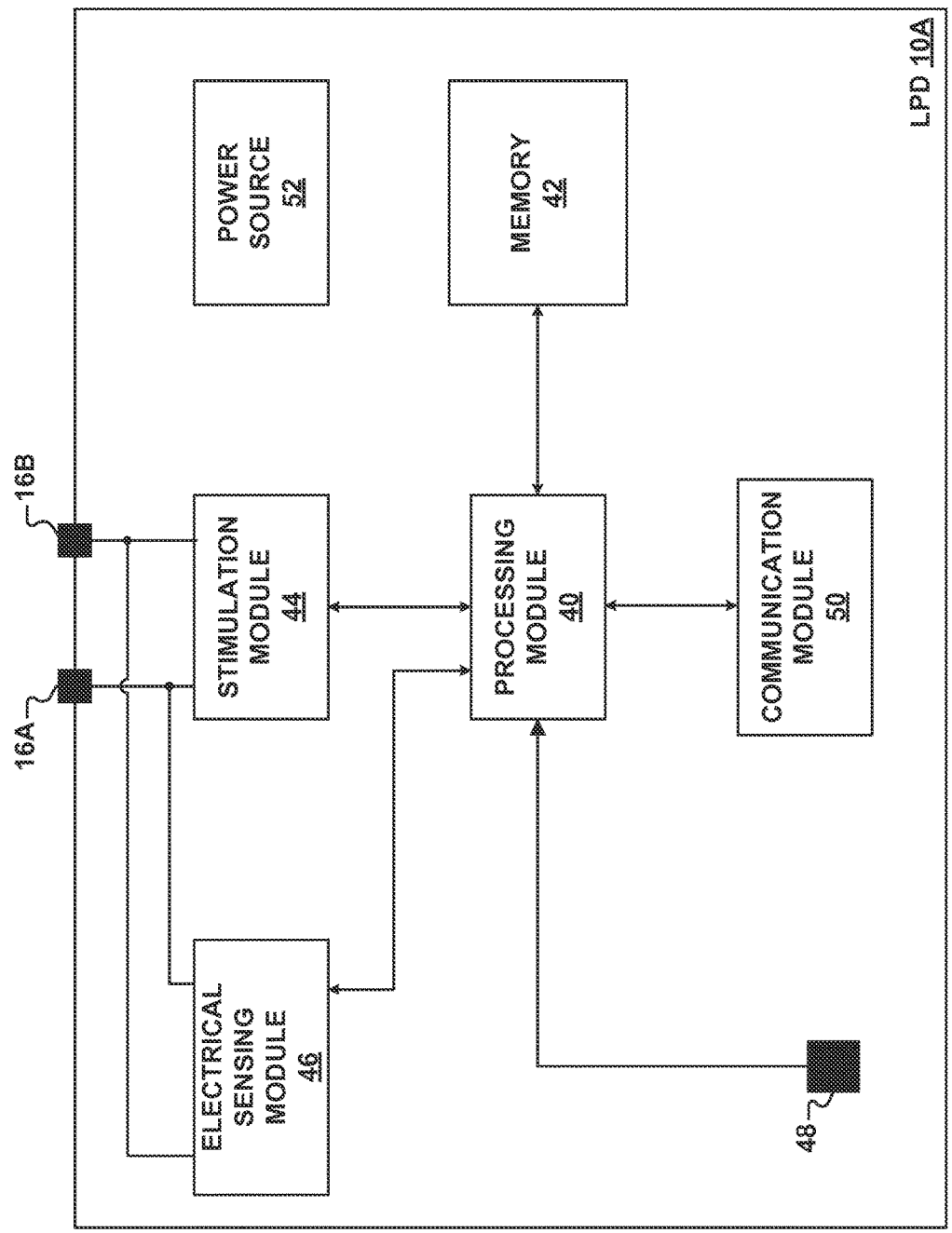
FIG. 4 is a functional block diagram illustrating an example configuration of the example leadless pacing device of FIG. 1.

FIG. 4 is a functional block diagram illustrating an example configuration of an LPD 10A configured to deliver atrio-ventricular synchronous pacing or asynchronous ventricular pacing in response to determining that no intrinsic ventricular activity was detected within a ventricular event detection window for at least one cardiac cycle and based on whether atrial oversensing is also detected. LPD 10B of FIGS. 3A and 3B may have a similar configuration as LPD 10A. However, electrode 16B of LPD 10A may be replaced by electrode 32 of LPD 10B, which may be positioned a greater distance away from electrode 16A and LPD 10B, as described above with respect to FIGS. 3A and 3B.

LPD 10A includes processing module 40, memory 42, stimulation module 44, electrical sensing module 46, sensor 48, communication module 50, and power source 52. Power source 52 may include a battery, e.g., a rechargeable or non-rechargeable battery.

Modules included in LPD 10A represent functionality that may be included in LPD 10A of the present disclosure. Modules of the present disclosure may include any discrete and/or integrated electronic circuit components that implement analog and/or digital circuits capable of producing the functions attributed to the modules herein. For example, the modules may include analog circuits, e.g., amplification circuits, filtering circuits, and/or other signal conditioning circuits. The modules may also include digital circuits, e.g., combinational or sequential logic circuits, memory devices, and the like. The functions attributed to the modules herein may be embodied as one or more processors, hardware, firmware, software, or any combination thereof. Depiction of different features as modules is intended to highlight different functional aspects, and does not necessarily imply that such modules must be realized by separate hardware or software components. Rather, functionality associated with one or more modules may be performed by separate hardware or software components, or integrated within common or separate hardware or software components.

Processing module 40 may include any one or more of a microprocessor, a controller, a digital signal processor (DSP), an application specific integrated circuit (ASIC), a field-programmable gate array (FPGA), or equivalent discrete or integrated logic circuitry. In some examples, processing module 40 includes multiple components, such as any combination of one or more microprocessors, one or more controllers, one or more DSPs, one or more ASICs, or one or more FPGAs, as well as other discrete or integrated logic circuitry. Additionally, although illustrated as separate functional components in FIG. 4, some or all of the functionality attributed to stimulation module 44, electrical sensing module 46, and communication module 50 may implemented in the one or more combination of one or more microprocessors, one or more controllers, one or more DSPs, one or more ASICs, one or more FPGAs, and/or other discrete or integrated logic circuitry that implements processing module 40.

Processing module 40 may communicate with memory 42. Memory 42 may include computer-readable instructions that, when executed by processing module 40, cause processing module 40 and any other modules of LPD 10A to perform the various functions attributed to them herein. Memory 42 may include any volatile, non-volatile, magnetic, or electrical media, such as a random access memory (RAM), read-only memory (ROM), non-volatile RAM (NVRAM), electrically-erasable programmable ROM (EEPROM), Flash memory, or any other memory device.

Stimulation module 44 and electrical sensing module 46 are electrically coupled to electrodes 16A, 16B. Processing module 40 is configured to control stimulation module 44 to generate and deliver pacing pulses to heart 24 (e.g., right ventricle 22 in the example shown in FIG. 2) via electrodes 16A, 16B. In addition, processing module 40 is configured to control electrical sensing module 46 to monitor an electrical signal from electrodes 16A, 16B in order to monitor electrical activity of heart 24. Electrical sensing module 46 may include circuits that acquire an electrical signal from electrodes 16A, 16B, as well as circuits to filter, amplify, and otherwise process the electrical signal. The electrical signal includes intrinsic cardiac electrical activity, such as depolarizations and repolarizations of the ventricles and depolarizations of the atria, and may be referred to as an electrical cardiac signal or a cardiac electrogram signal. Electrical sensing module 46 detects ventricular depolarizations, or ventricular activation events, within the electrical cardiac signal and detects atrial depolarizations, or atrial activation events, within the electrical cardiac signal.

In some examples, LPD 10A also includes sensor 48. In some examples, sensor 48 comprises one or more accelerometers. In some examples, sensor 48 comprises a plurality of accelerometers, e.g., three accelerometers, each of which is oriented to detect motion in the direction of a respective axis or vector. The axes or vectors may be orthogonal. In other examples, sensor 48 may comprises one or more different sensors that generate a signal as a function of motion, instead of or in addition to the one or more accelerometers, such as gyros, mercury switches, or bonded piezoelectric crystals. In other examples, sensor 48 may be a pressure sensor instead of one or more accelerometers.

Communication module 50 may include any suitable hardware (e.g., an antenna), firmware, software, or any combination thereof for communicating with another device, such as programmer 18 (FIGS. 2 and 3) or a patient monitor. Under the control of processing module 40, communication module 50 may receive downlink telemetry from and send uplink telemetry to other devices, such as programmer 18 or a patient monitor, with the aid of an antenna included in communication module 50.

Memory 42 may include data recorded by LPD 10A, e.g., electrical cardiac signals, heart rates, information regarding detection of atrial oversensing events or undersensing events, loss of conduction events, ventricular pacing efficacy, and the like. Under the direction of processing module 40, communication module 50 may transfer data recorded by LDP 10A to another device, such as programmer 18. Memory 42 may also store programming data received by processing module 40 from another device, such as programmer 18, via communication module 50. The programming data stored in memory 42 may include, as examples, lengths of any A-V intervals, lengths of any V-V intervals, atrial contraction detection delay periods, and atrial or ventricular activation event detection windows described herein. The programming data stored in memory 42 may additionally or alternatively include any threshold values described hereafter, such as for detecting atrial and/or ventricular contractions, determining whether pacing is efficacious, or determining whether atrio-ventricular synchronous pacing should be suspended in favor of asynchronous pacing. The programming data stored in memory 42 may additionally or alternatively include data used by processing module 40 to determine any values described herein, e.g., based determined parameters of heart 24, patient 26, or LPD 10A.

FIG. 5 is a timing diagram illustrating normal conduction timing in a heart of a patient. The amount of time between an atrial activation event (paced or sensed) and a subsequent ventricular activation event (paced or sensed) may be referred to herein as an "A-V interval." In FIG. 5, the A-V interval has a consistent value of T1, while the intervals between successive atrial events (i.e., the A-A interval) consistently have a value of T3. The interval between a ventricular activation event $V_{ACT}$ and a subsequent atrial activation event $A_{ACT}$ (i.e., the V-A interval) has a consistent value of T2, and the intervals between successive ventricular activation events (i.e., the V-V interval) may consistently have a value of T4. The values of T1-T4 may change over time as the heart rate of the patient changes.

FIG. 6 is a timing diagram illustrating an example technique for controlling LPD 10A (or another LPD) implanted in right ventricle 22 to switch from a sensing without pacing mode to an atrio-ventricular synchronous pacing mode in response to detecting loss of conduction, e.g., determining that no intrinsic ventricular activity was detected within a ventricular event detection window for at least one cardiac cycle. The timing diagram also illustrates an example technique for delivering atrio-ventricular synchronous pacing. An activation of an atrium may be an intrinsic or paced depolarization of the atrium, or a mechanical contraction of the atrium. Thus, processing module 40 may identify activation of an atrium by, for example, determining that electrical sensing module 46 detected an intrinsic depolarization of the atrium (e.g., a far field P-wave), by determining that another device (e.g., another LPD implanted in the atrium) delivered a pacing pulse to the atrium, or by detecting mechanical contraction of the atrium (e.g. using an accelerometer or another motion sensor).

In some examples, in a sensing without pacing mode, processing module 40 may detect atrial activation events $A_{ACT}$, e.g., in an electrical cardiac signal sensed by electrical sensing module 46 (FIG. 4), as well as ventricular sense events $V_S$ (e.g., R-waves), e.g., in the sensed electrical cardiac signal. The ventricular sense event $V_S$ may be the electrical activity associated with intrinsic depolarization of the ventricle (e.g., the right ventricle 22) in which LPD 10A is implanted. Processing module 40 may determine whether a ventricular sense event $V_S$ is detected within a ventricular event detection window $W_{VACT}$. In some examples, such as the one shown in FIG. 6A, ventricular event detection window $W_{VACT}$ begins at a prior detected an atrial activation event $A_S$. In other examples, such as when processing module 40 detects atrial oversensing, processing module 40 may start the ventricular event detection window $W_{VACT}$ at a prior detected ventricular sense event $V_S$ or at a time at which a ventricular sense is expected to occur, e.g., based on a stored heart rate (V-V interval). Detection of a ventricular sense event $V_S$ within ventricular event detection window $W_{VACT}$ may indicate that heart 24 is exhibiting normal intrinsic conduction.

In some examples, processing module 40 determines the duration of the ventricular event detection window $W_{VACT}$ based on the stored data that indicates the A-A interval for a predetermined number of most recent cardiac cycles (e.g., one to twelve beats). This historic A-A interval data may be stored by memory 42 or a memory of another device. In some examples, the duration of the ventricular event detection window $W_{VACT}$ may be one of: the mean A-A interval of the stored A-A intervals, the median A-A interval of the stored A-A intervals, the greatest A-A interval of the stored A-A intervals, the shortest A-A interval of the stored A-A intervals, or the most recent A-A interval of the stored A-A intervals. As another example, the duration of the ventricular event detection window $W_{VACT}$ may less than a historic A-A interval, as shown in FIG. 6A. For example, the duration of the ventricular event detection window $W_{VACT}$ may be a predetermined percentage of the stored A-A intervals, such as 30% to about 75% (e.g., about 50%) of the mean or median A-A interval for the last one to twelve beats.

In addition, or instead, the duration of the ventricular event detection window $W_{VACT}$ may be selected by a clinician and may be independent of the historic A-A interval data for the patient. For example, in some examples, the duration of the ventricular event detection window $W_{VACT}$ is preprogrammed to be a fixed duration between about 300 milliseconds (ms) to about 700 ms, such as about 500 ms. Processing module 40 may receive the ventricular event detection window $W_{VACT}$ from the clinician via, e.g., a medical device programmer 18 (FIG. 2) that is configured to communicate with LPD 10A.

In yet other examples, processing module 40 determines the duration of the ventricular event detection window $W_{VACT}$ based on the stored data that indicates the interval between successive atrial events (i.e., the A-A interval) for a certain number of most recent cardiac cycles and a preprogrammed duration. For example, processing module 40 may determine a first ventricular event detection window $W_{VACT}$ based on the stored A-A interval data, e.g., using the techniques described above, and may select the duration of the ventricular event detection window $W_{VACT}$ to be the smaller of the first ventricular event detection window $W_{VACT}$ and a fixed, programmed duration. In this way, at relatively slow heart rates, processing module 40 use the fixed, programmed duration as the ventricular event detection window $W_{VACT}$, and at higher heart rates, the duration that is based on the actual cardiac activity of patient 26 may be used.

In response to determining that, for a particular cardiac cycle, a ventricular sense event $V_S$ is detected within the ventricular event detection window $W_{VACT}$, processing module 40 may continue operating LPD 10A in the sensing without pacing mode for at least the next cardiac cycle. For example, as shown in FIG. 6A, processing module 40 detects atrial activation event 60A and a ventricular sense event 62A within a time period $T_5$ of atrial activation event 60A, the duration of time period $T_5$ being less than the duration of ventricular event detection window $W_{VACT}$. Atrial activation event 60A and ventricular sense event 62A are part of the same cardiac cycle. Thus, processing module 40 maintains the sensing without pacing mode for the next cardiac cycle. Processing module 40 detects a subsequent normal cardiac cycle in which processing module 40 detects, based on an electrical cardiac signal sensed by sensing module 46, ventricular sense event 62B within a ventricular event detection window $W_{VACT}$ of atrial activation event 60B.

During a next cardiac cycle in the example shown in FIG. 6A, processing module 40 detects ventricular sense event 62C within a ventricular event detection window $W_{VACT}$ of atrial activation event 60C. Processing module 40, however, detects multiple atrial activation events 60D-60F within an atrial event detection window $W_{AACT}$, which can be an expected interval between successive atrial events (A-A). In some examples, processing module 40 determines atrial event detection window $W_{AACT}$ based on the stored data that indicates the interval between successive atrial activation events (i.e., the A-A interval) for a predetermined number of most recent cardiac cycles (e.g., one to 12 beats). The atrial event detection window $W_{AACT}$ can be, for example, the mean A-A interval of the stored A-A intervals, the median A-A interval of the stored A-A intervals, the greatest A-A interval of the stored A-A intervals, the shortest A-A interval of the stored A-A intervals, or the most recent A-A interval of the stored A-A intervals.

Processing module 40 may, for example, detect each of the atrial activation events 60D-60F while implementing a stored atrial event detection algorithm, which may indicate amplitude thresholds of an electrical cardiac signal or a motion signal, timing relative to certain characteristics of an electrogram (e.g., a T-wave), and the like, associated with atrial activation events. Thus, processing module 40 may not include physiological noise (e.g., a far-field R-wave) known to not be indicative of an atrial activation in the atrial activation event count.

In response to detecting multiple atrial activation events 60D-60F within the atrial event detection window $W_{AACT}$, processing module 40 increments an atrial oversensing event counter or generates an atrial oversensing indication, which may be a flag, value, or other parameter stored by memory 42 of LPD 10A or another device, thereby indicating the occurrence of an atrial oversensing event. In some examples, processing module 40 only increments the counter or generates the indication in response to detecting a threshold number of atrial activation events $A_{ACT}$ within a single atrial event detection window $W_{AACT}$. The threshold number of atrial activation events within a single atrial event detection window $W_{AACT}$ can be, for example, two, three, or more than three. More than three atrial activation events may not be associated with any physiological condition, such that the threshold of three or more may indicate atrial oversensing is occurring due to a non-physiological reason, such as detected electrical noise.

In addition to, or instead of incrementing the counter based on whether a threshold number of atrial activation events $A_{ACT}$ within a single atrial event detection window $W_{AACT}$, processing module 40 may increment the counter in response to determining the atrial activation events detected within the single atrial event detection window $W_{AACT}$ have a rate greater than or equal to a rate threshold, which can be, for example, a programmable beats per minute. In some examples, the rate threshold is 150 beats per minute or greater.

The atrial oversensing event counter can be implemented by software, hardware, firmware, or any combination thereof. For example, when processing module 40 increments the counter, processing module 40 may generate a flag, value or other parameter or indication generated by processing module 40 and stored by memory 42 of LPD 10A or a memory of another device (e.g., another implanted device or an external medical device programmer). As another example, the counter may be implemented by a register-type circuit and processing module 40 may cause a state of the register-type circuit to change in order to increment or otherwise manage the counter. Counters having other configurations may also be used.

In some examples, the atrial oversensing event counter may count the number of successive cardiac cycles in which atrial oversensing was detected. In other examples, the counter may count the number of cardiac cycles ("X") out of a predetermined number of consecutive cardiac cycles ("Y") in which atrial oversensing was detected. This may be referred to as an "X of Y" type counter. "X" can be, for example, one, two, three, four or more in some examples. "Y" can be greater than or equal to "X" and can be, for example, three, four, five, six or more. In other examples, the atrial oversensing event counter may count the number of cardiac cycles, within a predetermined period of time, in which atrial oversensing was detected.

In a sensing without pacing mode, processing module 40 determines whether heart 24 of patient 26 is intrinsically conducting, such that ventricular pacing therapy is not merited. As noted above, processing module 40 may determine that heart 24 is intrinsically conducting by detecting a ventricular sense event $V_S$ within a ventricular event detection window $W_{VACT}$ that begins at an atrial activation event $A_{ACT}$, which may indicate that there is no A-V block and heart 24 is intrinsically conducting. When atrial oversensing occurs, however, processing module 40 may be unable to determine which, if any, of the detected atrial activation events $A_{ACT}$ 60D-60F is indicative of the time at which the atrium of heart 24 activated.

In examples described herein, when LPD 10A is operating in the sensing without pacing mode, detection of atrial oversensing by processing module 40 may not result in a change to the operating mode of LPD 10A unless the atrial oversensing is presented in combination with the detection of one or more ventricular activity events, which may indicate A-V block. For example, as long as processing module 40 continues to detect ventricular sense events $V_S$ at an expected time, which can be within a ventricular event detection window $W_{VACT}$ that begins at an atrial sense event or within a time window x that begins at a prior detected ventricular sense event $V_S$, processing module 40 may determine that heart 24 is intrinsically conducting, and no ventricular pacing therapy is desirable. As a result, the determination of which of the many detected atrial activation events actually corresponds to activation of the right atrium may not be required in order to control ventricular pacing therapy, because no ventricular pacing is being delivered.

In the example shown in FIG. 6A, in addition to incrementing the oversensing event counter, in response to detecting multiple atrial activation events 60D-60F within the atrial event detection window $W_{AACT}$, in order to determine whether A-V block is present, processing module 40 determines whether a ventricular sense event $V_S$ occurs within a first time period x that begins at the ventricular sense event 62C of the prior cardiac cycle.

In some examples, the first time period x is an expected time interval between successive naturally occurring (without the aid of ventricular pacing) ventricular sense events $V_S$, assuming the atrial activation rate of patient 26 stays relatively constant. For example, processing module 40 may determine the first time period x based on the stored data that indicates the interval between successive ventricular sense events (i.e., the V-V interval) for a predetermined number of most recent cardiac cycles (e.g., one to 12 beats). The first time period x can be, for example, the mean V-V interval of the stored V-V intervals, the median V-V interval of the stored V-V intervals, the greatest V-V interval of the stored V-V intervals, the shortest V-V interval of the stored V-V intervals, or the most recent V-V interval of the stored V-V intervals. In other examples, the first time period x may be an A-A interval, which is discussed above.

In the example shown in FIG. 6A, processing module 40 determines that a ventricular sense event $V_S$ 62D occurs within first time period x that begins at the ventricular sense event 62C of the prior cardiac cycle. Thus, processing module 40 determines that heart 24 is intrinsically conducting.

Processing module 40 subsequently detects multiple atrial activation events 60G, 60H within a next atrial event detection window $W_{AACT}$, which is shown as being within first time period x that begins at the ventricular sense event 62D of the prior cardiac cycle. In response, processing module 40 may increment the atrial oversensing event counter, and determine whether intrinsic A-V conduction is still present. In the example shown in FIG. 6A, processing 40 makes this determination by at least determining whether a ventricular sense event occurs within first time window x that begins at ventricular sense event 62D.

In response to determining a ventricular sense event $V_S$ did not occur within a time period x that begins at the ventricular sense event 62D, processing module 40 increments a loss of conduction counter or generates a loss of conduction indication, which may be a flag, value, or other parameter stored by memory 42 of LPD 10A or another device. As with the atrial oversensing event counter, the loss of conduction counter can be implemented by software, hardware, firmware, or any combination thereof.

As discussed above, in some examples, the loss of conduction counter may count the number of successive cardiac cycles in which a loss of conduction indication was generated or the counter may be an X of Y type counter. In other examples, the counter may count the number of cardiac cycles, within a predetermined period of time, in which no intrinsic ventricular activity was detected within a ventricular event detection window.

Processing module 40 is configured to determine, after incrementing the atrial oversensing event counter or the loss of conduction counter, the values of the counters. As discussed in further detail below, in response to determining the loss of conduction counter value is greater than or equal to a loss of conduction event threshold value and in response to determining the atrial oversensing event counter is less than or equal to the atrial oversensing event threshold value, processing module 40 may control LPD 10A to switch from the sensing without pacing mode to the atrio-ventricular synchronous pacing mode. The loss of conduction event threshold value may be, for example, one, while in other examples, the loss of conduction event threshold value may be more than one, such as two, three, or four or more.

In examples in which the loss of conduction event threshold value is more than one, the LPD may not switch to the atrio-ventricular synchronous pacing mode immediately after detection one cardiac cycle in which no intrinsic ventricular activity was detected within a ventricular event detection window. This may permit heart 24 of patient 26 to resume intrinsic conduction. In this way, LPD 10A may be configured to determine whether heart 24 resumes intrinsic conduction before delivering ventricular pacing therapy. This may promote better synchrony of heart 24 of patient 26 in at least some instances.

In the example shown in FIG. 6A, the loss of conduction event threshold value is greater than one. Thus, in response to determining a ventricular sense event $V_S$ did not occur within a time period x that begins at ventricular sense event 62D, processing module 40 does not immediately control stimulation module 44 (FIG. 4) to deliver a ventricular pacing pulse in the cardiac cycle in which the ventricular sense event $V_S$ was not detected. Instead, processing module 40 continues to monitor the cardiac activity in at least one more cardiac cycle to determine whether intrinsic ventricular activation occurs. As shown in FIG. 6A, processing module 40 may determine whether ventricular sense event $V_S$ is detected within a second time period y that that begins at the end of the first time period x. Thus, because no ventricular event is detected within the cardiac cycle that immediately follows the cardiac cycle including ventricular sense event 62D, heart 24 of patient 26 drops at least one beat. The dropping of the heart beat may permit processing module 40 to, for example, sense the intrinsic conduction of heart 24 and determine whether heart 24 returns to a normal cardiac rhythm without the aid of pacing therapy. In this way, processing module 40 may be configured to control pacing therapy by LPD 10A to favor intrinsic conduction.

In some examples, first time period x and second time period y may be substantially equal. In other examples, first time period x is greater than second time period y. For example, second time period y may be equal to the time period x minus the time period from an atrial sense event $A_S$ to a time at which stimulation module 44 would have delivered a ventricular pacing pulse in an atrio-ventricular pacing mode (SAV), plus an offset, such as 80 ms. Thus, in some examples, second time period y may be equal to x−SAV+OFFSET. A second time period y that is less than the first time period x may help provide more responsive cardiac pacing therapy because it may result in a more timely ventricular pacing pulse $V_P$ in the subsequent cardiac cycle.

In yet other examples, first time period x is less than second time period y. In these examples, the second time period y may be referred to as having a duration of "x+offset," where the offset may be greater than zero.

In the example shown in FIG. 6A, processing module 40 determines that no ventricular sense event $V_S$ occurred within the second time period y that began at the end of first time period x. In response, processing module 40 may increment the loss of conduction counter, determine the value of the counter, and, in response to determining the value is less than the loss of conduction event threshold value, processing module 40 may continue monitoring the electrical cardiac activity in at least one more cardiac cycle to determine whether intrinsic ventricular activation occurs and may not control stimulation module 44 (FIG. 4) to deliver a ventricular pacing pulse in the cardiac cycle in which the ventricular sense event $V_S$ was not detected.

In the example shown in FIG. 6A, however, processing module 40 determines that the value of the loss of conduction counter is greater than or equal to the loss of conduction event threshold value. Processing module 40 also determines that multiple atrial activation events 60I and 60J are detected within atrial event detection window $W_{AACT}$, which begins at the end of time period x, thereby indicating that atrial oversensing has occurred in the present cardiac cycle. Processing module 40 may increment the atrial oversensing event counter in response to detecting the cardiac cycle with atrial oversensing. After incrementing the atrial oversensing event counter, processing module 40 determines the value of the counter in order to determine whether to deliver pacing therapy in accordance with the atrio-ventricular synchronous pacing mode or the asynchronous ventricular pacing mode.

In the example shown in FIG. 6A, processing module 40 determines that the atrial oversensing event counter is less than the atrial oversensing event threshold value, and, as a result, processing module 40 determines that atrial oversensing is not occurring. In response to determining that the value of the loss of conduction counter is greater than or equal to the loss of conduction event threshold value and the value of the atrial oversensing event counter is less than the atrial oversensing event threshold value, such that loss of conduction detected but atrial oversensing is not, processing module 40 controls LPD 10A to switch to the atrio-ventricular synchronous pacing mode by at least controlling stimulation module 44 to deliver a ventricular pacing pulse $V_P$ 64A to right ventricle 22 of patient 26 (FIG. 2).

According to an example technique for delivering atrio-ventricular synchronous pacing shown in FIG. 6A, after processing module 40 determines that an intrinsic ventricular sense event $V_S$ is not detected within a time period x that begins at the prior ventricular pacing pulse $V_P$ 64A, or within ventricular event activation window $W_{VACT}$, processing module 40 may control stimulation module 44 to deliver ventricular pacing pulse $V_P$ 64B to a ventricle (e.g., right ventricle 22) of heart 24 a time period $T_6$ after a detected atrial activation event $A_{ACT}$ 60K. In the example shown in FIG. 6A, time period $T_6$ is an atrio-ventricular synchronous pacing interval, which may be greater than or equal to a stored A-V interval in order to give processing module 40 an opportunity to determine whether intrinsic A-V conduction is detected, such that the atrio-ventricular pacing may be ventricular inhibited pacing. For example, time period $T_6$ may be about 80 ms, although other time intervals may also be used in other examples.

In some examples, time period $T_6$ is preprogrammed, e.g., selected by a clinician. Example time periods $T_6$ include, for example, about 80 ms to about 300 ms range, such as about 130 ms, although other preprogrammed atrio-ventricular synchronous pacing intervals may be used in other examples.

Processing module 40 may control the duration of time $T_6$ between the detection of atrial activation $A_S$ and the delivery of the next ventricular pacing pulse $V_P$. In some examples, processing module 40 selects the duration of time period $T_6$ based on the $A_{ACT}$-$V_S$ interval of two or more prior cardiac cycles (e.g., two cardiac cycles, three cardiac cycles, or more), which may be the cardiac cycles immediately preceding cardiac cycles in which atrial oversensing was not detected and intrinsic ventricular activity was detected within a ventricular event detection window. For example, the duration of time period $T_6$ may be equal to the average $A_{ACT}$-$V_S$ interval of two or more prior cardiac cycles in which atrial oversensing was not detected and intrinsic ventricular activity was detected within a ventricular event detection window. The average $A_{ACT}$-$V_S$ interval may be better representative of the current heart rate of patient 26 than, for example, a preprogrammed atrio-ventricular synchronous pacing interval ($A_{ACT}$-$V_P$), which affects the pacing interval. Controlling the delivery of ventricular pacing pulse $V_P$ relative to an atrial activation event $A_{ACT}$ based on the average $A_{ACT}$-$V_S$ interval of the two or more preceding cardiac cycles may help smooth the heart rate of patient 26, particularly when compared to the delivery of atrio-ventricular synchronous pacing using a preprogrammed atrio-ventricular synchronous pacing interval ($A_{ACT}$-$V_P$).

In a next cardiac cycle, processing module 40 detects an atrial activation event 60L, determines whether a ventricular sense event is detected within a ventricular event detection window $W_{VACT}$ that begins at atrial activation event 60L, and, in response to determining the ventricular sense event as not detected within the ventricular event detection window $W_{VACT}$ or within a predetermined A-V interval, processing module 40 controls stimulation module 44 to deliver ventricular pacing pulse $V_P$ 64C to a ventricle (e.g., right ventricle 22) of heart 24 a time period $T_6$ after the detected atrial activation event $A_{ACT}$ 60L. However, if processing module 40 detects the ventricular sense event within the ventricular event detection window $W_{VACT}$ or the A-V interval, then processing module 40 may not control stimulation module 44 to deliver ventricular pacing in that particular cardiac cycle.

In some examples, once processing module 40 switches to the atrio-ventricular synchronous pacing mode, processing module 40 may apply a different ventricular event detection window $W_{VACT}$, which may be preprogrammed and associated with the atrio-ventricular synchronous pacing mode. For example, the ventricular event detection window $W_{VACT}$ applied during the atrio-ventricular synchronous pacing mode may be about 80 ms to about 300 ms such as about 130 ms, although other windows may also be used. Thus, in some examples of the technique shown in FIG. 6A, the ventricular event detection window $W_{VACT}$ used by processing module 40 in the cardiac cycles including atrial activation events 60K and 60L may differ from the one used during the cardiac cycle including atrial activation events 60A and 60B.

During operation in the atrio-ventricular synchronous pacing mode, processing module 40 may periodically perform an intrinsic conduction check to determine whether heart 24 has returned to normal intrinsic conduction. For example, processing module 40 may control stimulation module 44 to withhold ventricular pacing (Vp) for at least one cardiac cycle (e.g., one cardiac cycle, two cardiac cycles, or three or more cardiac cycles) in order to determine whether an intrinsic ventricular sense event $V_S$ is detected within a ventricular event detection window $W_{VACT}$ of an atrial activation event $A_{ACT}$.

In response to determining that an intrinsic ventricular sense event $V_S$ is not detected within a ventricular event detection window $W_{VACT}$ of an atrial activation event $A_{ACT}$, processing module 40 may continue to control stimulation module 44 deliver ventricular pacing pulses to right ventricle 22 in the atrio-ventricular synchronous pacing mode. However, as shown in FIG. 6B, in some examples in which processing module 40 detects an intrinsic ventricular sense event $V_S$ within the ventricular event detection window $W_{VACT}$ that begins at a respective atrial activation event $A_{ACT}$, processing module 40 may switch LPD 10A to the sensing without pacing mode.

Figure 6B:
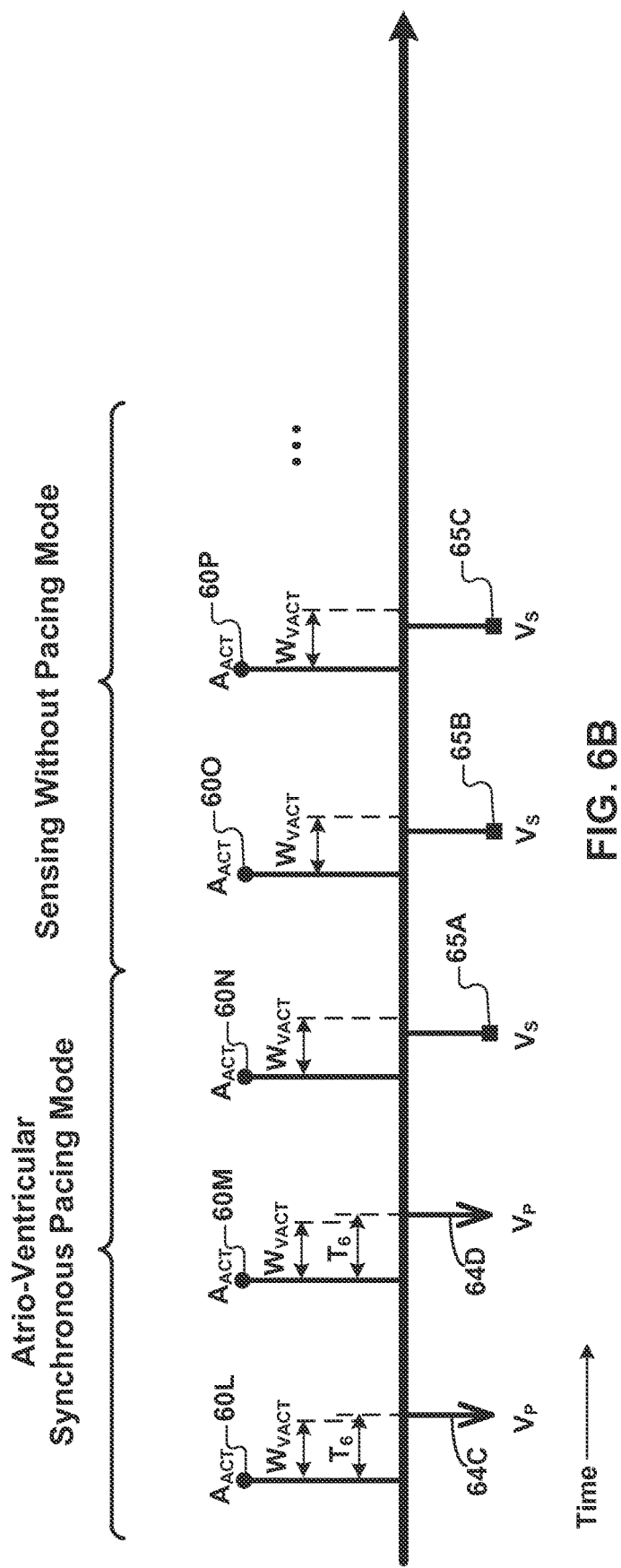
FIG. 6B is a timing diagram illustrating an example technique for controlling a leadless pacing device to switch from an atrio-ventricular synchronous pacing mode to a sensing without pacing mode.

FIG. 6B is a timing diagram that may follow the timing diagram shown in FIG. 6A. In FIG. 6B, after processing module 40 controls stimulation module 44 to deliver ventricular pacing pulse $V_P$ 64C to a ventricle (e.g., right ventricle 22) of heart 24 a time period $T_6$ after the detected atrial activation event $A_{ACT}$ 60, processing module 40 controls stimulation module 44 to deliver ventricular pacing pulse $V_P$ 64D to a ventricle (e.g., right ventricle 22) of heart 24 a time period $T_6$ after a detected atrial activation event $A_{ACT}$ 60M of a next cardiac cycle. In the next cardiac cycle, processing module 40 determines that an intrinsic ventricular sense event 65A is detected within ventricular event detection window $W_{VACT}$ that begins at atrial activation event 60N. Thus, processing module 40 may determine that conduction is present, and because atrial oversensing is also determined not to be occurring, processing module 40 may switch LPD 10 to the sensing without pacing mode. In the sensing without pacing mode, processing module 40 withholds the delivery of ventricular pacing pulses, as shown in the subsequent cardiac cycles in which processing module 40 detects ventricular sense event 65B within a ventricular event detection window $W_{VACT}$ of atrial activation event 60O, and detecting ventricular sense event 65C within a ventricular event detection window $W_{VACT}$ of atrial activation event 60P.

In other examples, processing module 40 may switch LPD 10A to the sensing without pacing mode in response to determining that, for a predetermined threshold number (e.g., stored by memory 42) of successive cardiac cycles, an intrinsic ventricular sense event Vs is detected within the ventricular event detection window $A_{ACT}$ of a respective atrial activation event $A_{ACT}$. The threshold number of cardiac cycles may be, for example, two, three, four, or more.

If after switching LPD 10A to the sensing without pacing mode, processing module 40 determines that loss of conduction begins occurring again, processing module 40 may switch LPD 10 to the atrio-ventricular synchronous pacing mode in response to detecting loss of conduction, but not atrial oversensing, or may switch LPD 10 to the a synchronous pacing mode in response to detecting loss of conduction and atrial oversensing, as discussed with respect to FIG. 6B.

In addition, in some examples, processing module 40 may switch LPD 10A to the sensing without pacing mode in response to determining intrinsic conduction was observed during an intrinsic conduction check. In some examples, to perform the intrinsic conduction check, processing module 40 temporarily places LPD 10A in a sensing without pacing mode for at least one cardiac cycle (e.g., one cardiac cycle, or two cardiac cycles). In response to determining intrinsic conduction was observed during at least one cardiac cycle, processing module 40 may control LPD 10A to stay in the sensing without pacing mode.

Processing module 40 may perform the intrinsic conduction check at any suitable interval, which may remain the same or may increase over time. For example, after switching to the atrio-ventricular synchronous pacing mode, processing module 40 may perform the conduction checks at progressive time intervals that increase over time. As an example, one minute after switching LPD 10A to the atrio-ventricular synchronous pacing mode, processing module 40 may perform an intrinsic conduction test. If no intrinsic conduction is tested, then processing module 40 may continue operating LPD 10A in the atrio-ventricular synchronous pacing mode, and perform an intrinsic conduction check two minutes after the first check. If no intrinsic conduction is detected at that point, then processing module 40 may continue operating LPD 10A in the atrio-ventricular synchronous pacing mode and perform another intrinsic conduction check four minutes after the second check. This may go on with any suitable progressively increasing time interval.

As discussed above, when both the atrial oversensing event counter value is less than or equal to an atrial oversensing event counter threshold value and the loss of conduction counter value is less than or equal to a ventricular activity event threshold value, LPD 10A remains in the sensing without pacing mode. FIG. 6A is a timing diagram illustrating an example scenario in which processing module 40A controls LPD 10A to switch from a sensing without pacing mode to an atrio-ventricular synchronous pacing mode in response to determining a value of a loss of conduction counter is greater than or equal to a loss of conduction event threshold value, when the atrial oversensing counter value is less than or equal to an atrial oversensing counter threshold value.

Figure 7A:
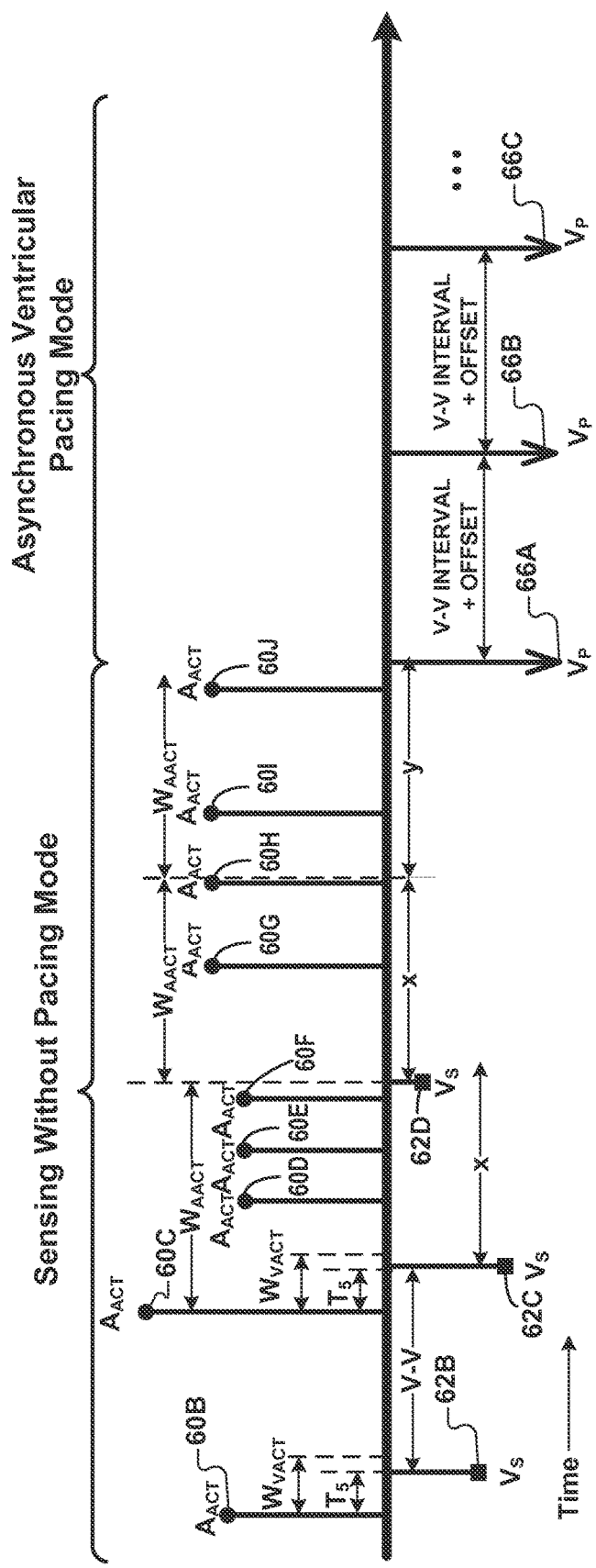
FIG. 7A is a timing diagram illustrating an example technique for controlling a leadless pacing device to switch from a sensing without pacing mode to an asynchronous ventricular pacing mode.

FIG. 7A is a timing diagram an example scenario in which processing module 40 controls LPD 10A to switch from a sensing without pacing mode to asynchronous ventricular pacing mode in response to determining a value of the loss of conduction counter is greater than or equal to the loss of conduction event threshold value and the atrial oversensing event counter value is greater than or equal to the atrial oversensing event counter threshold value. Processing module 40 may also control LPD 10A to switch to an asynchronous ventricular pacing mode when LPD 10A is operating in an atrio-ventricular synchronous pacing mode and processing module 40 determines the atrial oversensing event counter value is greater than or equal to the atrial oversensing event counter threshold value.

In the example shown in FIG. 7A, the sensing without pacing mode is the same as the sensing without pacing mode shown in FIG. 6A. However, after processing module 40 determines that no ventricular sense event $V_S$ occurred within the second time period y that began at the end of first time period x that began at ventricular sense event 62D, processing module 40 increments the loss of conduction counter, and subsequently determines the value of the loss of conduction counter is greater than or equal to the loss of conduction event threshold value. In addition, within the same cardiac cycle, processing module 40 determines that multiple atrial activation events 60I and 60J are detected within atrial event detection window $W_{AACT}$ that begins at the end of first time period x, increments the atrial oversensing event counter in response to detecting the cardiac cycles with atrial oversensing, and determines that the atrial oversensing event counter is greater than or equal to the atrial oversense event threshold value.

In response to determining that the value of the loss of conduction counter is greater than or equal to the loss of conduction event threshold value and the value of the atrial oversensing event counter is greater than or equal to the atrial oversensing event threshold value, processing module 40 controls LPD 10A to switch to the asynchronous ventricular pacing mode by at least controlling stimulation module 44 to deliver a ventricular pacing pulse $V_P$ 66A to right ventricle 22 of patient 26 (FIG. 2). Ventricular pacing pulse $V_P$ 66A is delivered at the end of second time period y.

In the asynchronous ventricular pacing mode, processing module 40 may determine whether an intrinsic depolarization of right ventricle 22 is detected within a within a V-V interval that begins when a ventricular activation was detected (e.g., $V_P$ 66A). If processing module 40 determined the intrinsic depolarization of right ventricle 22 was detected within the V-V interval, then processing module 40 may not control stimulation module 44 to deliver a ventricular pacing pulse $V_P$ 66B to right ventricle 22. On the other hand, in response to determining the intrinsic depolarization of right ventricle 22 was not detected within the V-V interval, processing module 40 may control stimulation module 44 to deliver a ventricular pacing pulse $V_P$ 66B to right ventricle 22.

In the example shown in FIG. 7A, the time period between successive pacing pulses 66A, 66B in the asynchronous ventricular pacing mode is shown as the V-V interval of one or more prior cardiac cycles, plus an offset (e.g., about 30 ms to about 150 ms, such as about 50 ms or about 100 ms, though it may vary based on the heart rate). In some examples, processing module 40 determines the V-V interval based on one or more prior cardiac cycles. For example, the V-V interval may be the average interval between ventricular activation events of the one or more prior cardiac cycles. The V-V interval may indicate the average or median heart rate, such that the offset results in a pacing rate that may be lower than the prior detected heart rate of patient 26.

Following the delivery of ventricular pacing pulse $V_P$ 66B, processing module 40 may determine whether an intrinsic depolarization of right ventricle 22 is detected within a within a V-V interval that begins at ventricular pacing pulse $V_P$ 66A. In response to determining the intrinsic depolarization of right ventricle 22 was not detected within the V-V interval, processing module 40 may control stimulation module 44 to deliver a ventricular pacing pulse $V_P$ 66C to right ventricle 22. On the other hand, if processing module 40 determines the intrinsic depolarization of right ventricle 22 was detected within the V-V interval, then processing module 40 may not control stimulation module 44 to deliver a ventricular pacing pulse $V_P$ 66C to right ventricle 22, such that ventricular pacing is inhibited.

After LPD 10A delivers ventricular pacing pulse $V_P$ 66C, processing module 40 may continue controlling LPD 10A to continue deliver ventricular pacing pulses in the asynchronous ventricular pacing mode. LPD 10A may intermittently sense atrial activation events, even when in the asynchronous ventricular pacing mode. In some situations, it may be desirable for LPD 10A to deliver atrio-ventricular synchronous pacing when possible in order to help heart 26 maintain synchrony. Thus, in some examples described herein, after processing module 40 controls LPD 10A to switch to an asynchronous ventricular pacing mode, processing module 40 may periodically determine whether atrial oversensing is occurring. For example, processing module 40 may sense atrial activation events and determine the number of atrial activation events occurring within a particular time range or determine the rate of atrial activation events. Processing module 40 may determine atrial oversensing is no longer occurring in response to determining the number of atrial activation events occurring within a particular time range or the rate of atrial activation events is less than or equal to an atrial oversensing threshold.

In response to determining an atrial oversensing is not occurring, but no intrinsic ventricular activity is detected within a ventricular event detection window for a threshold number of cardiac cycles, e.g., using the counters discussed above, processing module 40 may control LPD 10A to switch to the atrio-ventricular synchronous pacing mode, as shown in the timing diagram of FIG. 7B. An LPD 10A configured in this manner may deliver rate responsive pacing when the atrial rate is too slow or consistent atrial oversensing is occurring, while favoring AV synchronous pacing over asynchronous pacing. On other hand, in response to determining that atrial is not occurring and intrinsic ventricular activity is occurring, e.g., using the counters discussed above, processing module 40 may control LPD 10A to operate in the sensing without pacing mode, as shown in FIG. 7C.

As shown in FIG. 7B, if processing module 40 determines that atrial oversensing is no longer occurring, processing module 40 may control stimulation module 44 to deliver ventricular pacing pulse 70A to heart 24 in accordance with an atrio-ventricular synchronous pacing mode. In this mode, as shown in FIG. 7B and described above with respect to FIG. 6A, a ventricular pacing pulse is timed with respect to a prior atrial activation event. For example, as shown in FIG. 7B, ventricular pacing pulses 70A-70C are timed to respective atrial activation events 68A-68C.

As shown in FIG. 7C, if processing module 40 determines that atrial oversensing is no longer occurring and a threshold number of intrinsic ventricular activation events are detected within a ventricular event activation window $W_{V_{ACT}}$ (such that loss of conduction is no longer detected), then processing module 40 may control LPD 10A to operate in a sensing without pacing mode. For example, processing module 40 may detect atrial activation events 60O, 60P, determine whether an intrinsic ventricular sense event 65B, 65C is detected within a ventricular event activation window $W_{V_{ACT}}$ that begins at the respective atrial activation events 60O, 60P, and so forth.

In other examples of the technique shown in FIG. 7A, rather than controlling LPD 10A to switch to the asynchronous ventricular pacing mode after detecting the threshold number of cardiac cycles in which multiple atrial activation events are detected, processing module 40 may control LPD 10A to operate in a hybrid mode in which LPD 10A delivers ventricular pacing pulses 66A, 66B, 66C for at least a threshold number of cardiac cycles (e.g., three, four or more) according to the asynchronous ventricular pacing mode, while processing module 40 determines, based on the electrical cardiac signal sensed by sensing module 46, whether atrial oversensing continues to occur. Processing module 40 may, for example, reset the atrial oversensing event counter after stimulation module 44 delivers ventricular pacing pulse 66A, while still controlling stimulation module 44 to generate and deliver ventricular pacing pulses 66B, 66C. If, after determining that atrial oversensing is continuing to occur, e.g., based on the value of the atrial oversensing event counter, processing module 40 may control LPD 10A to switch to the asynchronous ventricular pacing mode.

Figure 8:
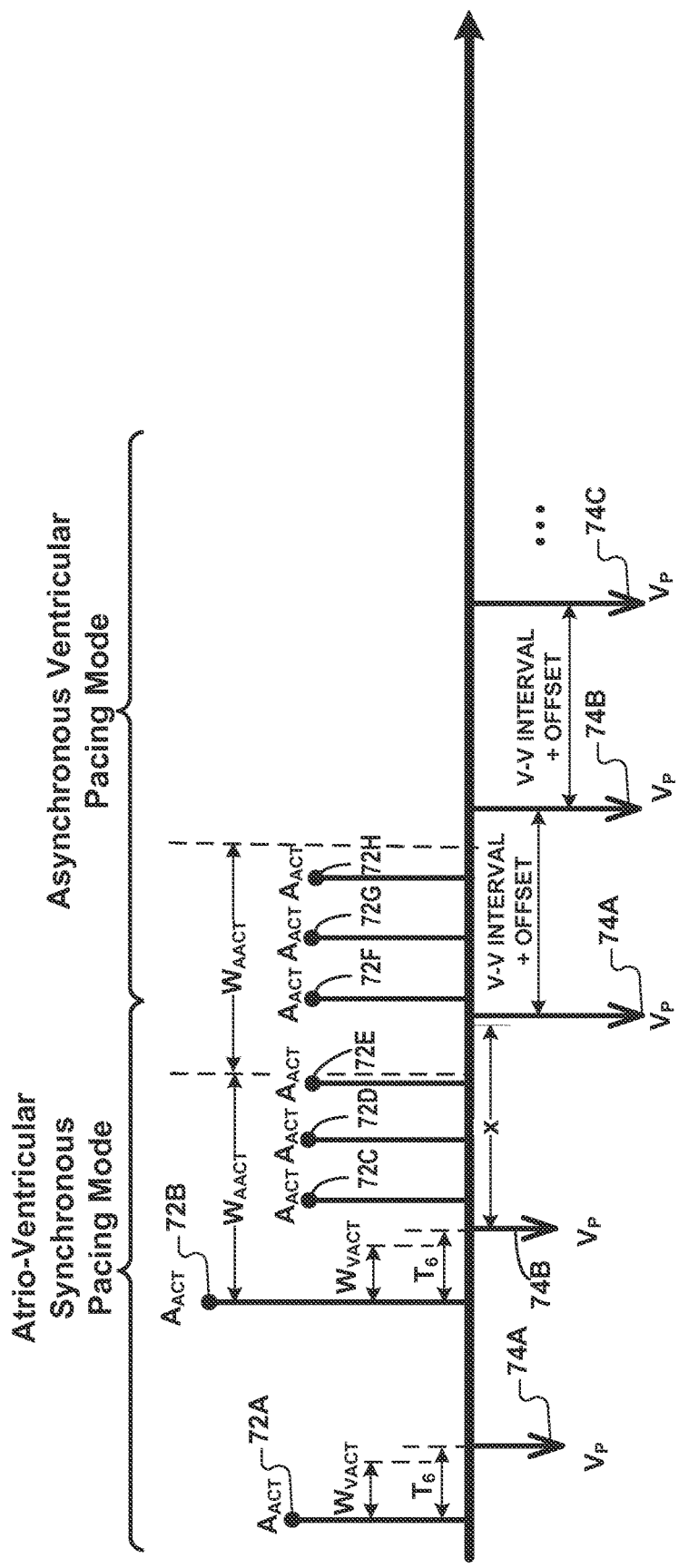
FIG. 8 is a timing diagram illustrating an example technique for controlling a leadless pacing device to switch from an atrio-ventricular synchronous pacing mode to an asynchronous ventricular pacing mode

In any of the examples described herein, processing module 40 may control LPD 10A to switch from an atrio-ventricular synchronous pacing mode to the asynchronous pacing mode in response to determining that atrial oversensing is occurring in conjunction with the intrinsic loss of conduction. FIG. 8 is an example timing diagram illustrating an example technique for controlling LPD 10A to switch from an atrio-ventricular synchronous pacing mode to an asynchronous ventricular pacing mode in response to detecting both atrial oversensing and loss of conduction.

While operating LPD 10A in an atrio-ventricular synchronous pacing mode, processing module 40 detects atrial activation event 72A, which may be an intrinsic or paced depolarization of the atrium, or a mechanical contraction of the atrium. Processing module 40 may determine whether a ventricular sense event is detected within a ventricular event detection window $W_{V_{ACT}}$ that begins at atrial activation event 72A. In response to determining no ventricular sense event is detected within the ventricular event detection window $W_{V_{ACT}}$, processing module 40 may control stimulation module 44 to deliver ventricular pacing pulse $V_P$ 74A. In a subsequent cardiac cycle, processing module 40 detects atrial activation event 72B, determine whether a ventricular sense event is detected within a ventricular event detection window $W_{V_{ACT}}$ that begins at atrial activation event 72B, and controls stimulation module 44 to deliver ventricular pacing pulse $V_P$ 74B in response to determining no ventricular sense event is detected within the ventricular event detection window $W_{V_{ACT}}$.

In the next cardiac cycle, processing module 40 detects multiple atrial activation events 72C, 72D, 72E within an atrial event detection window $W_{AACT}$ that begins at atrial activation event 72B of the immediately prior cardiac cycle, e.g., using the techniques described above with respect to FIG. 6A. In response to detecting multiple atrial activation events 60D-60F within the atrial event detection window $W_{AACT}$, processing module 40 increments an atrial oversensing event counter or generates an atrial oversensing indication. In some examples, processing module 40 only increments the counter or generates the indication in response to detecting a threshold number of atrial activation events $A_{ACT}$ within a single atrial event detection window $W_{AACT}$ and/or in response to determining the atrial activation events detected within the single atrial event detection window $W_{AACT}$ have a rate greater than or equal to a rate threshold.

Processing module 40 also determines whether a ventricular sense event $V_S$ occurs within a first time period x that begins at the ventricular pace event 74B of the prior cardiac cycle. If processing module 40 determines that a ventricular sense event $V_S$ occurs within first time period x, then processing module 40 may determine that heart 24 is intrinsically conducting and may switch LPD 10A to a sensing without pacing mode. On the other hand, in response to determining that a ventricular sense event $V_S$ occurs within first time period x, processing module 40 may control stimulation module 44 to deliver ventricular pacing pulse 74A.

Processing module 40 is configured to determine, after incrementing the atrial oversensing event counter, the values of the counters. In response to determining the loss of conduction counter value is than or equal to a loss of conduction event threshold value and the atrial oversensing event counter is less than or equal to the atrial oversensing event threshold value, processing module 40 may control LPD 10A to remain in the atrio-ventricular synchronous pacing mode. The atrial oversensing event threshold value may be, for example, one, two, three, four or more in different examples.

In the next cardiac cycle, processing module 40 detects multiple atrial activation events 72F, 72G, 72H within an atrial event detection window $W_{AACT}$ that begins at the end of the prior atrial event detection window $W_{AACT}$. In response, processing module 40 increments the atrial oversensing event counter, and, in the example shown in FIG. 8, determines that the atrial oversensing event counter is greater than or equal to the atrial oversensing event threshold value. In response to determining that the value of the atrial oversensing event counter is greater than or equal to the atrial oversensing event threshold value while processing module 40 is operating LPD 10A in the atrio-ventricular synchronous pacing mode, processing module 40 controls LPD 10A to switch to the asynchronous ventricular pacing mode by at least determining whether intrinsic depolarization of right ventricle 22 is detected within the V-V interval and, in response to determining intrinsic depolarization of right ventricle 22 is not detected within the V-V interval, controlling stimulation module 44 to deliver a ventricular pacing pulse 74B to right ventricle 22 of patient 26 (FIG. 2). Ventricular pacing pulse 74B is delivered at the end of a time period that begins at ventricular pacing pulse 74A (i.e., V-V interval+offset). A similar technique may be used to control the delivery of ventricular pacing pulse 74C.

Figure 9A:
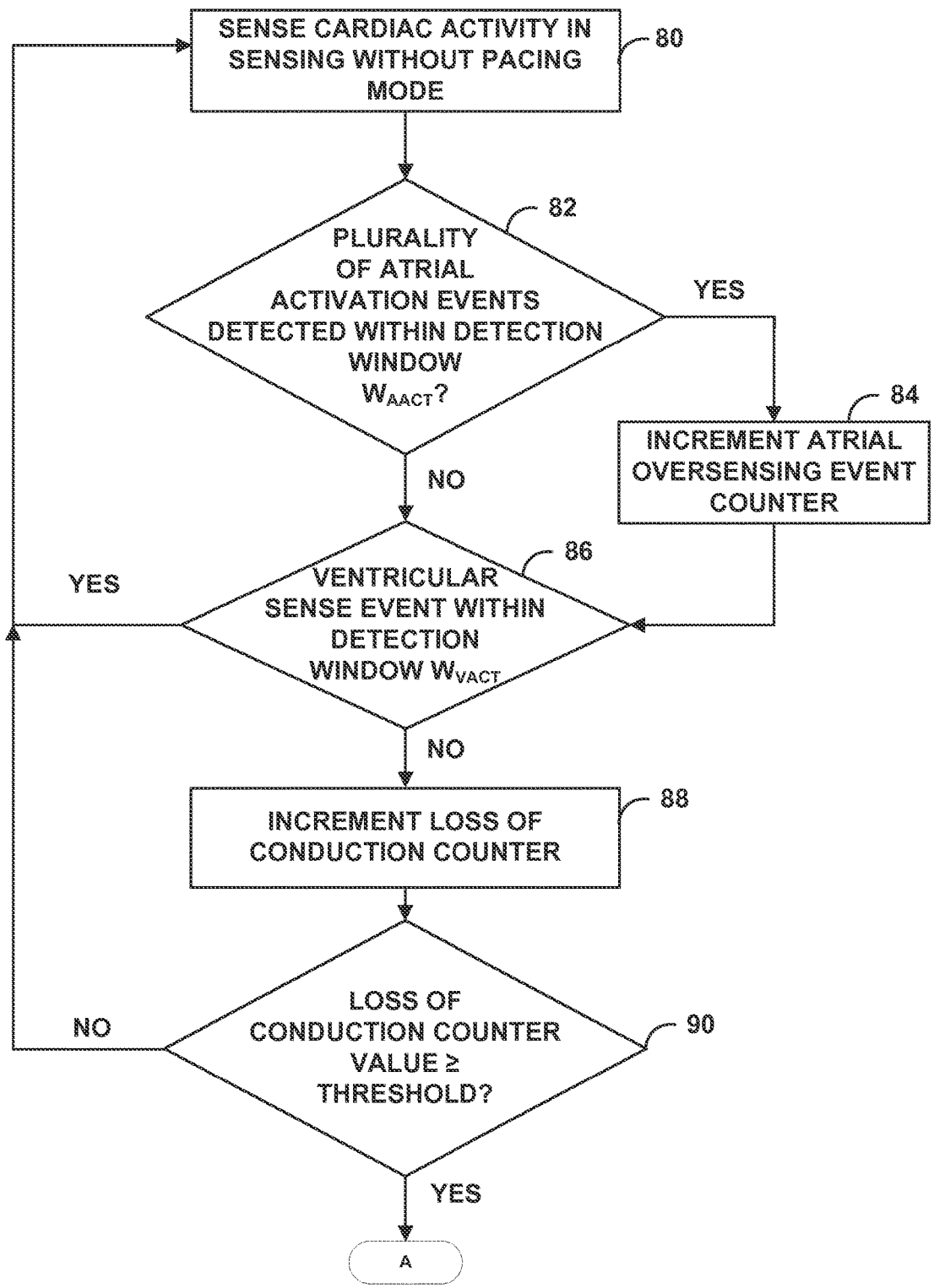
FIGS. 9A and 9B are a flow diagram of an example technique for controlling a leadless pacing device implanted in a ventricle of a heart to switch from a sensing without pacing mode to an atrio-ventricular synchronous pacing mode or an asynchronous ventricular pacing mode.
Figure 9B:
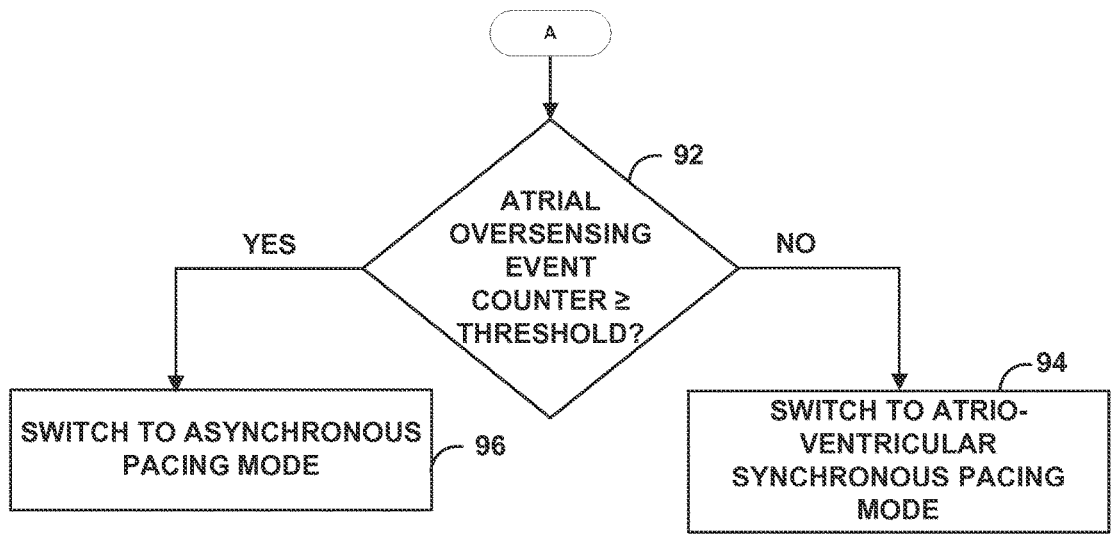

FIGS. 9A and 9B illustrate a flow diagram of an example technique for operating LPD 10A. In the technique shown in FIGS. 9A and 9B, processing module 40 switches LPD 10A from a sensing without pacing mode to an atrio-ventricular synchronous pacing mode in response to determining that no intrinsic ventricular activity was detected within a ventricular event detection window for at least one cardiac cycle and in response to determining atrial oversensing is not detected. In addition, in the technique shown in FIGS. 9A and 9B, processing module 40 switches LPD 10A from a sensing without pacing mode to an asynchronous ventricular pacing mode in response to detecting both loss of conduction and atrial oversensing.

While the technique shown in FIGS. 9A and 9B, as well as other techniques described herein, are primarily described as being performed by processing module 40, in other examples, the techniques described herein may be performed by another processing module (e.g., a processing module of another implanted device or an external device, such as a medical device programmer), alone or in combination with processing module 40. In addition, while right atrium 28 and right ventricle 22 are primarily referred to herein, in other examples, the devices, systems, and techniques described herein may also be used to control pacing therapy delivered to the left ventricle, to sense activity of the left atrium, or both.

In accordance with the technique shown in FIGS. 9A and 9B, processing module 40 controls sensing module 46 of LPD 10A to sense an electrical cardiac signal in a sensing without pacing mode (80). Processing module 40 determines whether a plurality of atrial activation events $A_S$ are detected within an atrial event detection window $W_{AACT}$ (82), which, as discussed with respect to FIG. 6A, may begin at an immediately preceding atrial activation event $A_{ACT}$ or at the end of first time period x (shown in FIGS. 6A-7C).

In response to determining a plurality of atrial activation events $A_S$ are detected within the detection window $W_{AACT}$ ("YES" branch of block 82) processing module 40 increments an atrial oversensing event counter (84). In examples in which the atrial oversensing event counter counts successive cardiac cycles in which atrial oversensing is detected, processing module 40 may reset the counter in response to determining the multiple atrial activation events $A_S$ are not detected within the detection window $W_{AACT}$. If an "X of Y" type counter is used, however, then processing module 40 may update the number of cardiac cycles, "Y," to include the most recent cardiac cycle and update the number of cardiac cycles in which multiple atrial activation events were detected, "X," within the Y number of cardiac cycles accordingly. As another example, processing module 40 may manage the atrial oversensing event counter to track the number of cardiac cycles in which multiple atrial activation events were detected for a predetermined range of time (e.g., within 30 seconds, one minute or more), and may update the counter value accordingly.

After incrementing the atrial oversensing event counter or in response to determining a plurality of atrial activation events $A_S$ are not detected within a ventricular event detection window $W_{VACT}$ ("NO" branch of block 82), processing module 40 determines whether a ventricular sense event is detected within a ventricular event detection window $W_{VACT}$ (86). In response to determining the ventricular sense event is detected within the ventricular event detection window $W_{VACT}$ ("YES" branch of block 86), processing module 40 continues to operate LPD 10A in the sensing without pacing mode.

In examples in which the loss of conduction counter counts successive cardiac cycles in which no ventricular sense event is detected, processing module 40 may reset the counter in response to determining the ventricular sense event is detected within the ventricular event detection window $W_{VACT}$. If an "X of Y" type counter is used, however, then processing module 40 may update the number of cardiac cycles, "Y," to include the most recent cardiac cycle and update the number of cardiac cycles in which no ventricular activation event was detected, "X," within the Y number of cardiac cycles accordingly. As another example, processing module 40 may manage the loss of conduction counter to track the number of cardiac cycles in which a ventricular activation event was not detected for a predetermined range of time (e.g., within 30 seconds, one minute or more), and may update the counter value accordingly.

In some examples of the technique shown in FIGS. 9A and 9B, processing module 40 may generate a loss of conduction indication in response to determining a ventricular sense event was not detected within the detection window $W_{VACT}$ and may increment the loss of conduction counter by storing the ventricular event indication in memory 42 of LPD 10A or a memory of another device. Processing module 40 may reset the ventricular event counter by deleting the stored loss of conduction indications. Processing module 40 may also determine whether the ventricular event counter value is greater than or equal to the threshold value (90) by at least determining whether the number of stored ventricular event indications is greater than or equal to the ventricular event threshold value.

In response to determining the ventricular sense event is not detected within the ventricular event detection window $W_{VACT}$ ("NO" branch of block 86), processing module 40 increments a loss of conduction counter (88). After incrementing the loss of conduction counter (88), processing module 40 determines whether the value of the loss of conduction counter is greater than or equal to a loss of conduction event threshold value (90). The loss of conduction event threshold value, as well as other threshold values discussed herein, may be stored by memory 42 of LPD 10A or a memory of another device.

In some examples, the loss of conduction event threshold value is one. In other examples, the loss of conduction event threshold value may be greater than one, such as two, three, or four or more. The loss of conduction event threshold value may be value determined by a clinician to be indicative of a loss of intrinsic AV conduction, and may be selected to be low enough to configure LPD 10A to provide a responsive switch in operation mode, and to provide responsive cardiac rhythm management therapy.

In response to determining the value of the loss of conduction counter is not less than the loss of conduction event threshold value (or not less than or equal to the threshold value in some examples) ("NO" branch of block 90), processing module 40 determines that intrinsic ventricular activity is being detected, and, therefore, continues to operate LPD 10A in the sensing without pacing mode.

In response to determining the value of the loss of conduction counter is greater than or equal to the loss of conduction event threshold value (or greater than the threshold value in some examples) ("YES" branch of block 90), processing module 40 determines that loss of conduction is occurring and pacing therapy may be desirable. Thus, in order to determine which pacing mode to use, processing module 40 determines whether atrial oversensing is also occurring. In the example shown in FIGS. 9A and 9B, processing module 40 makes this determination based on the value of atrial oversensing event counter. If atrial oversensing is not occurring, processing module 40 may determine that the delivery of ventricular pacing pulses can be timed to atrial activation events, such that ventricular pacing should be delivered in accordance with the atrio-ventricular synchronous pacing mode. Thus, in response to determining the value of the atrial oversensing event counter is less than the atrial oversensing event threshold value (or, in some examples, less than or equal to the threshold value) ("NO" branch of block 92), processing module 40 controls LPD 10A to begin delivering ventricular pacing pulses in the atrio-ventricular synchronous pacing mode (94). In some examples, the atrial oversensing event threshold value is one. In other examples, the atrial oversensing event threshold value may be greater than one, such as two, three, or four or more.

On the other hand, if both loss of conduction and atrial oversensing are occurring, processing may determine that the delivery of ventricular pacing pulses should not be timed to atrial activation events, but, rather, ventricular pacing should be delivered in accordance with the asynchronous ventricular pacing mode. Thus, in response to determining the value of the atrial oversensing event counter is greater than or equal to the atrial oversensing event threshold value (or, in some examples, greater than the threshold value) ("YES" branch of block 92), processing module 40 controls LPD 10A to begin delivering ventricular pacing pulses in the asynchronous ventricular pacing mode (96).

In some examples, processing module 40 controls LPD 10A to switch back to the sensing without pacing mode (or the atrio-ventricular synchronous pacing mode if LPD 10A was in the atrio-ventricular synchronous pacing mode prior to switching to the asynchronous ventricular pacing mode) after a predetermined number of cardiac cycles (e.g., two, three, or four, or five cardiac cycles) or after a predetermined period of time. This may enable processing module 40 to check for intrinsic A-V conduction and to determine whether atrial oversensing is continuing to occur. If atrial oversensing continues to occur after switching LPD 10A to the sensing without pacing mode or the atrio-ventricular synchronous pacing mode, however, e.g., after three cardiac cycles, then processing module 40 may control LPD 10A to make a dedicated switch to the asynchronous ventricular pacing mode for a longer period of time than the predetermined period of time.

In some examples of the technique shown in FIGS. 9A and 9B, processing module 40 may generate an atrial oversensing event indication in response to determining a multiple atrial activation events were detected within the detection window $W_{AACT}$ and may increment the atrial oversensing event counter by storing the atrial oversensing event indication in memory 42 of LPD 10A or a memory of another device. Processing module 40 may reset the atrial oversensing event counter by deleting the stored atrial oversensing event indications. Processing module 40 may also determine whether the atrial oversensing event counter value is greater than or equal to the threshold value (92) by at least determining whether the number of stored ventricular event indications is greater than or equal to the ventricular event threshold value.

The configuration of LPD 10A described with respect to FIGS. 6A, 6B, and 7A, in which LPD 10A does not deliver ventricular pacing in the cardiac cycle in which a ventricular event was not detected by processing module 40, may permit electrical sensing module 46 to sense the intrinsic activity of heart 24 for at least one full beat before delivering a ventricular pacing pulse. In this way, processing module 40 may take the time to sense the ventricular activation event, e.g., to permit heart 24 to resume intrinsic conduction, before LPD 10A delivers a ventricular pacing pulse, which may or may not correspond to the current heart rhythm of patient 26. By being configured to drop one or more heart beats, LPD 10A may be configured to promote the intrinsic conduction of heart 24 by giving LPD 10A the opportunity to sense intrinsic conduction of heart 24 before stimulation module 44 delivers ventricular pacing. This may help heart 24 stay synchronized.

Figure 10:
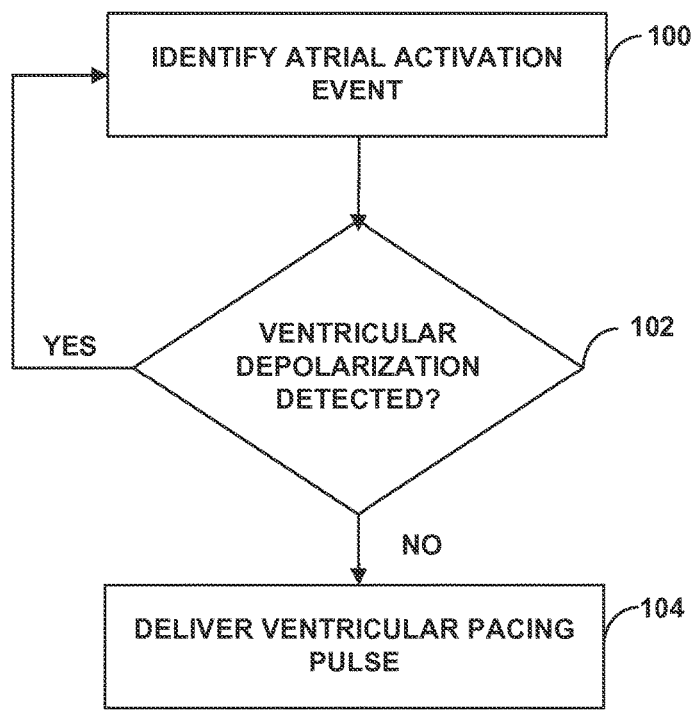
FIG. 10 is a flow diagram of an example technique for delivering pacing pulses to a ventricle of a heart in accordance with an atrio-ventricular synchronous pacing mode.

FIG. 10 is a flow diagram of an example technique for delivering pacing pulses to a ventricle of heart 24 in accordance with an atrio-ventricular synchronous pacing mode. Processing module 40 identifies an atrial activation event (100), which can be a sense or pace event, and determines whether an intrinsic ventricular sense event $V_S$ (e.g., an R-wave) is detected subsequent to the atrial activation event (102), e.g., within an A-V interval beginning when the atrial activation event was detected or within a ventricular event detection window $W_{VACT}$.

In response to determining the ventricular sense event was not detected subsequent to the atrial activation event ("NO" branch of block 84), processing module 40 may control stimulation module 44 to generate and deliver a pacing pulse to right ventricle 22 of heart 24 (104). In response to determining the ventricular sense event was detected subsequent to the atrial activation event ("YES" branch of block 84), LPD 10A may not deliver a ventricular pacing pulse, but, rather, processing module 40 may continue to monitor the cardiac activity of patient 26 (100, 102). For patients with intermittent AV node conduction, it may be preferable to inhibit ventricular pacing by LPD 10A in accordance with the technique shown in FIGS. 9A and 9B and allow an intrinsic ventricular depolarization to occur for a time, e.g., the A-V interval, after an intrinsic atrial depolarization or atrial pace.

In some examples, LPD 10A may oversense atrial activation events, which may affect the delivery of ventricular pacing pulses when LPD 10A is operating in the atrio-ventricular synchronous pacing mode. In accordance with some examples described herein, LPD 10A is configured to automatically switch (without user intervention in some cases) from the atrio-ventricular synchronous pacing mode to an asynchronous ventricular pacing mode in response to detecting atrial oversensing, e.g., based on the value of an atrial oversensing event counter, as discussed above with respect to FIGS. 9A and 9B.

Figure 11:
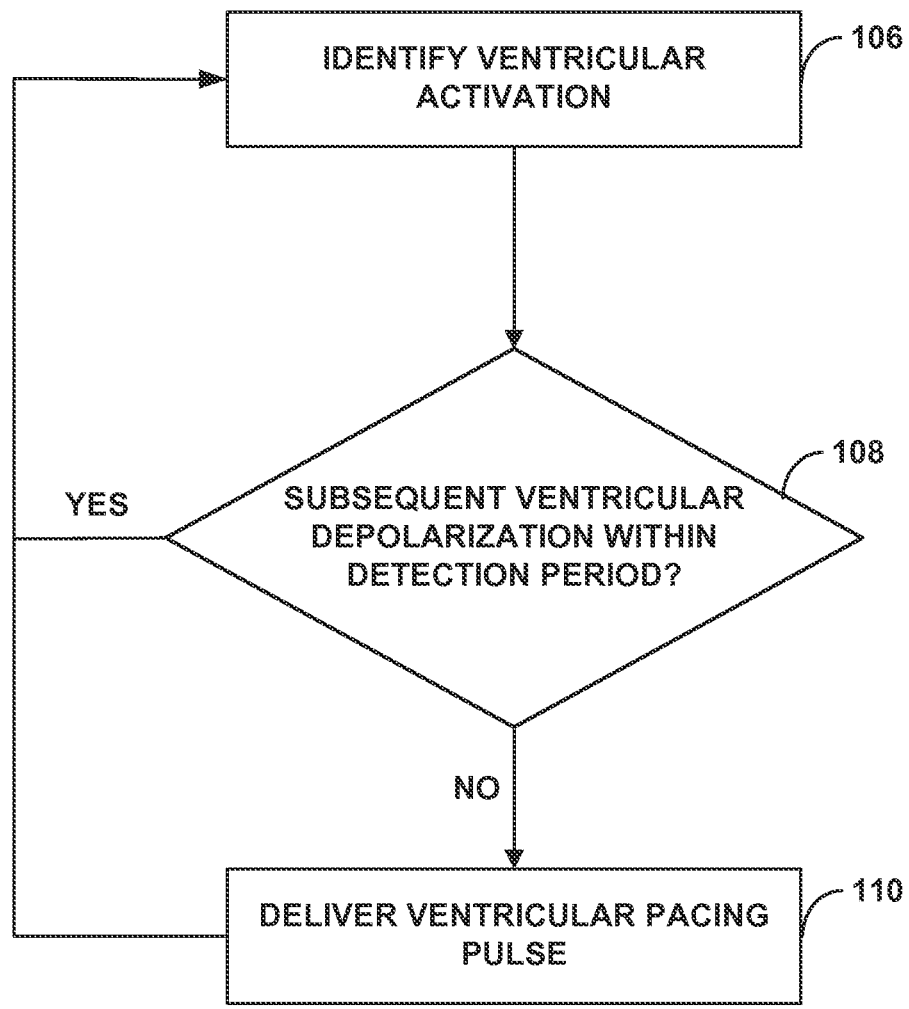
FIG. 11 is a flow diagram of an example technique for delivering pacing pulses to a ventricle of a heart in accordance with an asynchronous ventricular pacing mode.

FIG. 11 is a flow diagram of an example technique for delivering asynchronous ventricular pacing. In the technique shown in FIG. 11, processing module 40 identifies a ventricular activation event $V_{ACT}$ (106), which may be a delivery of a ventricular pacing pulse or an intrinsic depolarization of right ventricle 22 (e.g., an R-wave in an electrical cardiac signal sensed by sensing module 46). Processing module 40 determines whether an intrinsic depolarization of right ventricle 22 is detected within a within a V-V interval that begins when the ventricular activation was detected (e.g., when the previous intrinsic ventricular depolarization was detected, or a previous ventricular pacing pulse was delivered) (108).

The V-V interval may have any suitable length. In some examples, processing module 40 determines the V-V interval based on sensed cardiac activity of patient 26 and stores in the interval in memory 42. For example, processing module 40 may determine the V-V interval to be the average or median time between consecutive ventricular activation events (e.g., consecutive intrinsic ventricular depolarizations detected by electrical sensing module 44) for a certain number of cardiac cycles immediately preceding the present cardiac cycle. The certain number can be, for example, two or more, such as six, ten, twelve, twenty, or thirty. In some examples, processing module times the delivery of ventricular pacing pulses delivered in the asynchronous ventricular pacing mode using the V-V interval. In this case, the V-V interval may be slightly longer than the heart rate of patient 26, which may be determined from data from a sensor.

In other examples, processing module 40 may use a preprogrammed V-V interval. This, however, may be lower than the patient's current heart rate, which may cause a relatively abrupt change in the heart rate of patient 26, which may not be desired. Controlling the timing of ventricular pacing pulse $V_P$ delivered in accordance with the asynchronous ventricular pacing mode based on the V-V interval determined based on sensed cardiac activity of patient 26 may help smooth the heart rate of patient 26, particularly when compared controlling the timing of the pacing pulses based on a preprogrammed rate.

In some examples, processing module 40 determines the V-V interval to be the greater of the V-V interval determined based on sensed cardiac activity of patient 26 or a preprogrammed rate. This may enable processing module 40 to provide some minimum pacing rate, which may further help smooth the heart rate of patient 26.

In any of the examples described above, processing module 40 may also modify the V-V interval based on detected changes in the heart rate of patient 26. For example, processing module 40 may increase the V-V interval as heart rate decreases, and decrease the V-V interval as the heart rate increases. In this way, processing module 40 may provide rate adaptive asynchronous ventricular pacing.

In response to determining the intrinsic depolarization of right ventricle 22 was detected within the V-V interval ("YES" branch of block 108), processing module 40 may determine the sensed intrinsic depolarization of right ventricle 22 was a ventricular activation (106) and determine whether a subsequent intrinsic depolarization of right ventricle 22 is detected within a within a V-V interval (108).

In response to determining the intrinsic depolarization of right ventricle 22 was not detected within the V-V interval ("NO" branch of block 108), processing module 40 may control stimulation module 44 to deliver a ventricular pacing pulse to right ventricle 22 (110). Stimulation module 44 may deliver the ventricular pacing pulse at the end of the V-V interval that begins at the prior detected ventricular activation event $V_S$.

The techniques described in this disclosure, including those attributed to image IMD 16, programmer 24, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims. For example, the following Items are illustrative of further embodiments:

Item 1. A method comprising:
  detecting, by a processing module of a leadless pacing device, atrial oversensing while the leadless pacing device is in a sensing without pacing mode;
  determining, by the processing module and based on an electrical cardiac signal, whether intrinsic ventricular activity is occurring in conjunction with the atrial oversensing;
  in response to determining intrinsic ventricular activity is occurring in conjunction with the atrial oversensing, controlling, by the processing module, the leadless pacing device to continue operating in the sensing without pacing mode; and
  in response to determining intrinsic ventricular activity is not occurring in conjunction with the atrial oversensing, controlling, by the processing module, the leadless pacing device to deliver a ventricular pacing pulse to the patient according to an asynchronous ventricular pacing mode.

Item 2. The method of item 1, wherein detecting atrial oversensing comprises:
  comparing a value of an atrial oversensing event counter to an atrial oversensing event threshold value; and
  detecting atrial oversensing in response to determining the value is greater than or equal to the atrial oversensing event threshold value.

Item 3. The method of any of items 1-2, wherein detecting atrial oversensing comprises:
  detecting, by the processing module and based on the electrical cardiac signal, a ventricular sense event or an end of a ventricular activation event detection window; and
  detecting, by the processing module and based on the electrical cardiac signal, a plurality of atrial activation events within an atrial activation event detection window that begins at the ventricular sense event or at the end of the ventricular activation event detection window.

Item 4. The method of any of items 1-3, further comprising:
  incrementing a counter in response to detecting the plurality of atrial activation events within the atrial activation event detection window;
  comparing a value of the counter to a threshold value; and
  detecting atrial oversensing in response to determining the value of the counter is greater than or equal to the threshold value.

Item 5. The method of any of items 1-4, wherein the threshold value is two, three or four.

Item 6. The method of any of items 1-5, wherein the counter is configured to count a number of cardiac cycles in which multiple atrial activation events are detected from among a predetermined number of consecutive cardiac cycles.

Item 7. The method of any of items 1-6, wherein the counter is configured to count a number of cardiac cycles, within a predetermined time window, in which multiple atrial activation events are detected.

Item 8. The method of any of items 1-7, wherein the counter is configured to count a successive number of cardiac cycles in which multiple atrial activation events are detected.

Item 9. The method of any of items 1-8, wherein detecting the plurality of atrial activation events comprises detecting a plurality of P-waves in the sensed electrical cardiac signal or detecting the plurality of atrial activation events based on a signal indicative of mechanical motion of the atrium.

Item 10. The method of any of items 1-9, wherein determining whether intrinsic ventricular activity is occurring comprises:
  comparing a value of a loss of conduction counter to a loss of conduction event threshold value, the loss of conduction counter being incremented in response to a ventricular sense event not being detected within a ventricular event detection window; and determining intrinsic ventricular activity is occurring in response to determining the value is less than or equal to the loss of conduction event threshold value.

Item 11. The method of any of items 1-10, wherein determining whether intrinsic ventricular activity is occurring comprises:
  detecting, by the processing module and based on the electrical cardiac signal, a ventricular sense event or an end of a first ventricular activation event detection window; and
  determining, by the processing module and based on the electrical cardiac signal, a ventricular activation event is detected within a second ventricular activation event detection window that begins at the ventricular sense event or at the end of the first atrial event detection window.

Item 12. The method of any of items 1-11, further comprising:
  incrementing a counter in response to determining no ventricular activation event is detected within the second ventricular activation event detection window;
  comparing a value of the counter to a threshold value; and
  determining intrinsic ventricular activity is occurring response to determining the value of the counter is less than or equal to the threshold value.

Item 13. The method of any of items 1-12, wherein the threshold value is two, three or four.

Item 14. The method of any of items 1-13, wherein the counter is configured to count a number of cardiac cycles of a predetermined number of cardiac cycles in which no ventricular sense event is detected.

Item 15. The method of any of items 1-14, wherein the counter is configured to count a number of cardiac cycles, within a predetermined time window, in which no ventricular sense event is detected.

Item 16. The method of any of items 1-15, wherein the counter is configured to count a successive number of cardiac cycles in which no ventricular sense event is detected.

Item 17. The method of any of items 1-16, wherein controlling, by the processing module, the leadless pacing device to deliver the ventricular pacing pulse to the patient according to the asynchronous ventricular pacing mode comprises:
  detecting a ventricular activation event;
  determining whether intrinsic depolarization of the ventricle is detected within a detection window that begins at the ventricular activation event; and in response to determining that intrinsic depolarization of the ventricle is not detected within the detection window, controlling the leadless pacing device to deliver a pacing pulse to the ventricle.

Item 18. The method of any of items 1-17, wherein detecting the ventricular activation event comprises detecting a plurality of ventricular activation events, the method further comprising determining an average V-V interval based on the plurality of ventricular activation events and controlling the leadless pacing device to deliver pacing pulses according to the asynchronous ventricular pacing mode at a rate equal to the average V-V interval plus an offset.

Item 19. A leadless pacing system comprising:
a leadless pacing device configured to sense an electric cardiac signal and configured to operate in a sensing without pacing mode and an asynchronous ventricular pacing mode; and
a processing module configured to:
detect atrial oversensing while the leadless pacing device is in a sensing without pacing mode,
determine, based on the electrical cardiac signal, whether intrinsic ventricular activity is occurring in conjunction with the atrial oversensing,
in response to determining intrinsic ventricular activity is occurring in conjunction with the atrial oversensing, control the leadless pacing device to continue operating in the sensing without pacing mode, and
in response to determining intrinsic ventricular activity is not occurring in conjunction with the atrial oversensing, control the leadless pacing device to deliver a ventricular pacing pulse to the patient according to an asynchronous ventricular pacing mode.

Item 20 The system of any of item 19, wherein the processing module is configured to detect atrial oversensing by at least:
comparing a value of an atrial oversensing event counter to an atrial oversensing event threshold value, and
detecting atrial oversensing in response to determining the value is greater than or equal to the atrial oversensing event threshold value.

Item 21. The system of any of items 19-20, wherein the processing module is configured to detect atrial oversensing by at least:
detecting, based on the electrical cardiac signal, a ventricular sense event or an end of a ventricular activation event detection window, and
detecting, based on the electrical cardiac signal, a plurality of atrial activation events within an atrial activation event detection window that begins at the ventricular sense event or at the end of the ventricular activation event detection window.

Item 22. The system of any of items 19-21, wherein the processing module is further configured to increment a counter in response to detecting the plurality of atrial activation events within the atrial activation event detection window, compare a value of the counter to a threshold value, and detect atrial oversensing in response to determining the value of the counter is greater than or equal to the threshold value.

Item 23. The system of any of items 19-22, wherein the threshold value is two, three or four.

Item 24. The system of any of items 19-23, wherein the counter is configured to count a number of cardiac cycles in which multiple atrial activation events are detected from among a predetermined number of consecutive cardiac cycles.

Item 25. The system of any of items 19-24, wherein the counter is configured to count a number of cardiac cycles, within a predetermined time window, in which multiple atrial activation events are detected.

Item 26. The system of any of items 19-25, wherein the counter is configured to count a successive number of cardiac cycles in which multiple atrial activation events are detected.

Item 27. The system of any of items 19-26, wherein the processing module is configured to detect the plurality of atrial activation events by at least detecting a plurality of P-waves in the sensed electrical cardiac signal or detecting the plurality of atrial activation events based on a signal indicative of mechanical motion of the atrium.

Item 28. The system of any of items 19-27, wherein the processing module is configured to determine whether intrinsic ventricular activity is occurring by at least:
comparing a value of a loss of conduction counter to a loss of conduction event threshold value, the loss of conduction counter being incremented in response to a ventricular sense event not being detected within a ventricular event detection window, and determining intrinsic ventricular activity is occurring in response to determining the value is less than or equal to the loss of conduction event threshold value.

Item 29. The system of any of items 19-28, wherein the processing module is configured to determine whether intrinsic ventricular activity is occurring by at least:
detecting, based on the electrical cardiac signal, a ventricular sense event or an end of a first ventricular activation event detection window, and
determining, based on the electrical cardiac signal, a ventricular activation event is detected within a second ventricular activation event detection window that begins at the ventricular sense event or at the end of the first atrial event detection window.

Item 30. The system of any of items 19-29, wherein the processing module is further configured to increment a counter in response to determining no ventricular activation event is detected within the second ventricular activation event detection window, compare a value of the counter to a threshold value, and determine intrinsic ventricular activity is occurring response to determining the value of the counter is less than or equal to the threshold value.

Item 31. The system of any of items 19-30, wherein the threshold value is two, three or four.

Item 32. The system of any of items 19-31, wherein the counter is configured to count a number of cardiac cycles of a predetermined number of cardiac cycles in which no ventricular sense event is detected.

Item 33. The system of any of items 19-32, wherein the counter is configured to count a number of cardiac cycles, within a predetermined time window, in which no ventricular sense event is detected.

Item 34. The system of any of items 19-33, wherein the counter is configured to count a successive number of cardiac cycles in which no ventricular sense event is detected.

Item 35. The system of any of items 19-34, wherein the processing module is configured to control the leadless pacing device to deliver the ventricular pacing pulse to the patient according to the asynchronous ventricular pacing mode by at least:
detecting a ventricular activation event,
determining whether intrinsic depolarization of the ventricle is detected within a detection window that begins at the ventricular activation event, and in response to determining that intrinsic depolarization of the ventricle is not detected within the detection window, controlling the leadless pacing device to deliver a pacing pulse to the ventricle.

Item 36. The system of any of items 19-35, wherein the processing module is configured to detect a plurality of ventricular activation events, determine an average V-V interval based on the plurality of ventricular activation events, control the leadless pacing device to deliver pacing pulses according to the asynchronous ventricular pacing mode at a rate equal to the average V-V interval plus an offset.

Item 37. A system comprising:
means for detecting atrial oversensing while a leadless pacing device is in a sensing without pacing mode;
means for determining, based on an electrical cardiac signal, whether intrinsic ventricular activity is occurring in conjunction with the atrial oversensing;
means for controlling the leadless pacing device to continue operating in the sensing without pacing mode in response to determining intrinsic ventricular activity is occurring in conjunction with the atrial oversensing; and
means for controlling the leadless pacing device to deliver a ventricular pacing pulse to the patient according to an asynchronous ventricular pacing mode in response to determining intrinsic ventricular activity is not occurring in conjunction with the atrial oversensing.

Item 38. The system of item 37, further comprising counting means, wherein the means for detecting atrial oversensing compares a value of the counting means to an atrial oversensing event threshold value, and detects atrial oversensing in response to determining the value is greater than or equal to the atrial oversensing event threshold value.

Item 39. A computer-readable storage medium comprising instructions that, when executed by a processing module, cause the processing module to:
detect atrial oversensing while a leadless pacing device is in a sensing without pacing mode;
determine, based on an electrical cardiac signal, whether intrinsic ventricular activity is occurring in conjunction with the atrial oversensing;
in response to determining intrinsic ventricular activity is occurring in conjunction with the atrial oversensing, control the leadless pacing device to continue operating in the sensing without pacing mode; and
in response to determining intrinsic ventricular activity is not occurring in conjunction with the atrial oversensing, control the leadless pacing device to deliver a ventricular pacing pulse to the patient according to an asynchronous ventricular pacing mode.

Item 40. A method comprising:
detecting, by a processing module and based on an electrical cardiac signal sensed by a leadless pacing device while the leadless pacing device is in a sensing without pacing mode, loss of conduction of a heart of a patient;
determining, by the processing module, whether atrial oversensing is occurring in conjunction with the loss of conduction;
in response to determining the atrial oversensing is not occurring in conjunction with the loss of conduction, controlling, by the processing module, the leadless pacing device to deliver ventricular pacing pulses to the patient according to an atrio-ventricular synchronous pacing mode; and
in response to determining the atrial oversensing is occurring in conjunction with the loss of conduction, controlling, by the processing module, the leadless pacing device to deliver ventricular pacing pulses to the patient according to an asynchronous ventricular pacing mode.

Item 41. The method of item 40, further comprising, after controlling the leadless pacing device to deliver ventricular pacing pulses to the patient according to an atrio-ventricular synchronous pacing mode:
detecting, by the processing module, atrial oversensing based on the electrical cardiac signal while the leadless pacing device is delivering ventricular pacing pulses to the patient according to the atrio-ventricular synchronous pacing mode; and
in response to detecting atrial oversensing while the leadless pacing device is delivering ventricular pacing pulses to the patient according to the atrio-ventricular synchronous pacing mode, controlling, by the processing module, the leadless pacing device to deliver ventricular pacing pulses to the patient according to the asynchronous ventricular pacing mode.

Item 42. The method of any of items 40-41, wherein determining whether atrial oversensing is occurring in conjunction with the loss of conduction comprises:
comparing a value of an atrial oversensing event counter to an atrial oversensing event threshold value; and
detecting atrial oversensing in response to determining the value is greater than or equal to the atrial oversensing event threshold value.

Item 43. The method of any of items 40-42, wherein determining whether atrial oversensing is occurring in conjunction with the loss of conduction comprises:
detecting, by the processing module and based on the electrical cardiac signal, a ventricular sense event or an end of a ventricular activation event detection window; and
detecting, by the processing module and based on the electrical cardiac signal, a plurality of atrial activation events within an atrial activation event detection window that begins at the ventricular sense event or at the end of the ventricular activation event detection window.

Item 44. The method of any of items 40-43, further comprising:
incrementing a counter in response to detecting the plurality of atrial activation events within the atrial activation event detection window;
comparing a value of the counter to a threshold value; and
detecting atrial oversensing in response to determining the value of the counter is greater than or equal to the threshold value.

Item 45. The method of any of items 40-44, wherein the threshold value is two, three or four.

Item 46. The method of any of items 40-45, wherein detecting the plurality of atrial activation events comprises detecting a plurality of P-waves in the sensed electrical cardiac signal or detecting the plurality of atrial activation events based on a signal indicative of mechanical motion of the atrium.

Item 47. The method of any of items 40-46, wherein detecting loss of conduction comprises:
comparing a value of a loss of conduction counter to a loss of conduction event threshold value, the loss of conduction counter being incremented by the processing module in response to a ventricular sense event not being detected within a ventricular event detection window; and
determining intrinsic ventricular activity is occurring in response to determining the value is less than or equal to the loss of conduction event threshold value.

Item 48. The method of any of items 40-47, wherein detecting loss of conduction comprises:

detecting, by the processing module and based on the electrical cardiac signal, a ventricular sense event or an end of a first ventricular activation event detection window; and determining, by the processing module and based on the electrical cardiac signal, a ventricular activation event is not detected within a second ventricular activation event detection window that begins at the ventricular sense event or at the end of the first atrial event detection window.

Item 49. The method of any of items 40-48, further comprising:

incrementing a counter in response to determining no ventricular activation event is detected within the second ventricular activation event detection window;

comparing a value of the counter to a threshold value; and detecting loss of conduction in response to determining the value of the counter is greater than or equal to the threshold value.

Item 50. The method of any of items 40-49, wherein the threshold value is two, three or four.

Item 51. The method of any of items 40-50, wherein controlling, by the processing module, the leadless pacing device to deliver the ventricular pacing pulse to the patient according to the atrio-ventricular synchronous pacing mode comprises:

detecting an atrial activation event;

determining whether intrinsic depolarization of the ventricle is detected within a detection window that begins at the atrial activation event; and in response to determining that intrinsic depolarization of the ventricle is not detected within the detection window, controlling the leadless pacing device to deliver a pacing pulse to the ventricle.

Item 52. The method of any of items 40-51, wherein controlling, by the processing module, the leadless pacing device to deliver the ventricular pacing pulse to the patient according to the asynchronous ventricular pacing mode comprises:

detecting a ventricular activation event;

determining whether intrinsic depolarization of the ventricle is detected within a detection window that begins at the ventricular activation event; and in response to determining that intrinsic depolarization of the ventricle is not detected within the detection window, controlling the leadless pacing device to deliver a pacing pulse to the ventricle.

Item 53. A leadless pacing system comprising:

a leadless pacing device configured to sense an electric cardiac signal and configured to operate in a sensing without pacing mode, an atrio-ventricular pacing mode, and an asynchronous ventricular pacing mode; and a processing module configured to:

detect loss of conduction of a heart of a patient based on the electrical cardiac signal, determine whether atrial oversensing is occurring in conjunction with the loss of conduction, in response to determining the atrial oversensing is not occurring in conjunction with the loss of conduction, control the leadless pacing device to deliver ventricular pacing pulses to the patient according to an atrio-ventricular synchronous pacing mode, and in response to determining the atrial oversensing is occurring in conjunction with the loss of conduction, control the leadless pacing device to deliver ventricular pacing pulses to the patient according to an asynchronous ventricular pacing mode.

Item 54. The system of item 53, wherein the processing module is configured to, after controlling the leadless pacing device to deliver ventricular pacing pulses to the patient according to an atrio-ventricular synchronous pacing mode:

detect atrial oversensing based on the electrical cardiac signal while the leadless pacing device is delivering ventricular pacing pulses to the patient according to the atrio-ventricular synchronous pacing mode, and in response to detecting atrial oversensing while the leadless pacing device is delivering ventricular pacing pulses to the patient according to the atrio-ventricular synchronous pacing mode, control the leadless pacing device to deliver ventricular pacing pulses to the patient according to the asynchronous ventricular pacing mode.

Item 55. The system of any of items 53-54, wherein the processing module is configured to determine whether atrial oversensing is occurring in conjunction with the loss of conduction by at least:

comparing a value of an atrial oversensing event counter to an atrial oversensing event threshold value, and detecting atrial oversensing in response to determining the value is greater than or equal to the atrial oversensing event threshold value.

Item 56. The system of any of items 53-55, wherein the processing module is configured to determine whether atrial oversensing is occurring in conjunction with the loss of conduction by at least:

detecting, based on the electrical cardiac signal, a ventricular sense event or an end of a ventricular activation event detection window, and detecting, based on the electrical cardiac signal, a plurality of atrial activation events within an atrial activation event detection window that begins at the ventricular sense event or at the end of the ventricular activation event detection window.

Item 57. The system of any of items 53-56, wherein the processing module is further configured to increment a counter in response to detecting the plurality of atrial activation events within the atrial activation event detection window, compare a value of the counter to a threshold value, and detect atrial oversensing in response to determining the value of the counter is greater than or equal to the threshold value.

Item 58. The system of any of items 53-57, wherein the threshold value is two, three or four.

Item 59. The system of any of items 53-58, wherein the processing module is configured to detect the plurality of atrial activation events by at least detecting a plurality of P-waves in the sensed electrical cardiac signal or detecting the plurality of atrial activation events based on a signal indicative of mechanical motion of the atrium.

Item 60. The system of any of items 53-59, wherein the processing module is configured to detect loss of conduction by at least:

comparing a value of a loss of conduction counter to a loss of conduction event threshold value, the loss of conduction counter being incremented by the processing module in response to a ventricular sense event not being detected within a ventricular event detection window, and determining intrinsic ventricular activity is occurring in response to determining the value is less than or equal to the loss of conduction event threshold value.

Item 61. The system of any of items 53-61, wherein the processing module is configured to detect loss of conduction by at least:

detecting, based on the electrical cardiac signal, a ventricular sense event or an end of a first ventricular activation event detection window, and determining, based on the electrical cardiac signal, a ventricular activation event is not detected within a second ventricular activation event detection window that begins at the ventricular sense event or at the end of the first atrial event detection window.

Item 62. The system of any of items 53-61, wherein the processing module is further configured to increment a counter in response to determining no ventricular activation event is detected within the second ventricular activation event detection window, compare a value of the counter to a threshold value, and detect loss of conduction in response to determining the value of the counter is greater than or equal to the threshold value.

Item 63. The system of any of items 53-62, wherein the threshold value is two, three or four.

Item 64. The system of any of items 53-63, wherein the processing module is configured to control the leadless pacing device to deliver the ventricular pacing pulse to the patient according to the atrio-ventricular synchronous pacing mode by at least:

detecting an atrial activation event, determining whether intrinsic depolarization of the ventricle is detected within a detection window that begins at the atrial activation event, and in response to determining that intrinsic depolarization of the ventricle is not detected within the detection window, controlling the leadless pacing device to deliver a pacing pulse to the ventricle.

Item 65. The system of any of items 53-64, wherein the processing module is configured to control the leadless pacing device to deliver the ventricular pacing pulse to the patient according to the asynchronous ventricular pacing mode by at least:

detecting a ventricular activation event, determining whether intrinsic depolarization of the ventricle is detected within a detection window that begins at the ventricular activation event, and in response to determining that intrinsic depolarization of the ventricle is not detected within the detection window, controlling the leadless pacing device to deliver a pacing pulse to the ventricle.

Item 66. A system comprising:

means for detecting, based on an electrical cardiac signal sensed by a leadless pacing device while the leadless pacing device is in a sensing without pacing mode, loss of conduction of a heart of a patient;

means for determining whether atrial oversensing is occurring in conjunction with the loss of conduction;

means for the leadless pacing device to deliver ventricular pacing pulses to the patient according to an atrio-ventricular synchronous pacing mode in response to determining the atrial oversensing is not occurring in conjunction with the loss of conduction; and means for controlling the leadless pacing device to deliver ventricular pacing pulses to the patient according to an asynchronous ventricular pacing mode in response to determining the atrial oversensing is occurring in conjunction with the loss of conduction, controlling.

Item 67. The system of item 66, further comprising:

means for detecting atrial oversensing based on the electrical cardiac signal while the leadless pacing device is delivering ventricular pacing pulses to the patient according to the atrio-ventricular synchronous pacing mode; and means for controlling the leadless pacing device to deliver ventricular pacing pulses to the patient according to the asynchronous ventricular pacing mode in response to detecting atrial oversensing while the leadless pacing device is delivering ventricular pacing pulses to the patient according to the atrio-ventricular synchronous pacing mode.

Item 68. A computer-readable storage medium comprising instructions that, when executed by a processing module, cause the processing module to:

detect, based on an electrical cardiac signal sensed by a leadless pacing device while the leadless pacing device is in a sensing without pacing mode, loss of conduction of a heart of a patient;

determine whether atrial oversensing is occurring in conjunction with the loss of conduction;

in response to determining the atrial oversensing is not occurring in conjunction with the loss of conduction, control the leadless pacing device to deliver ventricular pacing pulses to the patient according to an atrio-ventricular synchronous pacing mode; and in response to determining the atrial oversensing is occurring in conjunction with the loss of conduction, control the leadless pacing device to deliver ventricular pacing pulses to the patient according to an asynchronous ventricular pacing mode.

What is claimed is:

1. A method comprising:

sensing an electrical cardiac signal;

detecting, by a processing module of a leadless pacing device, atrial oversensing while the leadless pacing device is in a sensing without pacing mode;

determining, by the processing module and based on the electrical cardiac signal, whether intrinsic ventricular activity is occurring in conjunction with the atrial oversensing;

when the determined intrinsic ventricular activity is occurring in conjunction with the atrial oversensing, controlling, by the processing module, the leadless pacing device to continue operating in the sensing without pacing mode; and when the determined intrinsic ventricular activity is not occurring in conjunction with the atrial oversensing, controlling, by the processing module, the leadless pacing device to deliver a ventricular pacing pulse to the patient according to an asynchronous ventricular pacing mode.

2. The method of claim 1, wherein detecting atrial oversensing comprises:

incrementing a value of an atrial oversensing event counter to track an atrial oversensing metric;

comparing the value of the atrial oversensing event counter to an atrial oversensing event threshold value; and detecting atrial oversensing in response to determining the value is greater than or equal to the atrial oversensing event threshold value.

3. The method of claim 2, wherein incrementing the value of the atrial oversensing event counter to track an atrial oversensing metric comprises incrementing the value of the atrial oversensing event counter to count the number of successive cardiac cycles in which atrial oversensing was detected.

4. The method of claim 2, wherein incrementing the value of the atrial oversensing event counter to track an atrial oversensing metric comprises incrementing the value of the atrial oversensing event counter to count the number of cardiac cycles out of a predetermined number of consecutive cardiac cycles in which atrial oversensing was detected.

5. The method of claim 2, wherein incrementing the value of the atrial oversensing event counter to track an atrial oversensing metric comprises incrementing the value of the atrial oversensing event counter to count the number of cardiac cycles, within a predetermined period of time, in which atrial oversensing was detected.

6. The method of claim 1, wherein detecting atrial oversensing comprises:
   detecting, by the processing module and based on the electrical cardiac signal, a ventricular sense event; and
   detecting, by the processing module and based on the electrical cardiac signal, a plurality of atrial activation events within an atrial activation event detection window that begins at the ventricular sense event.

7. The method of claim 6, further comprising:
   incrementing a counter in response to detecting the plurality of atrial activation events within the atrial activation event detection window;
   comparing a value of the counter to a threshold value; and
   detecting atrial oversensing in response to determining the value of the counter is greater than or equal to the threshold value.

8. The method of claim 7, wherein the threshold value is two, three or four.

9. The method of claim 7, wherein the counter is configured to count a number of cardiac cycles in which multiple atrial activation events are detected from among a predetermined number of consecutive cardiac cycles.

10. The method of claim 7, wherein the counter is configured to count a number of cardiac cycles, within a predetermined time window, in which multiple atrial activation events are detected.

11. The method of claim 7, wherein the counter is configured to count a successive number of cardiac cycles in which multiple atrial activation events are detected.

12. The method of claim 6, wherein detecting the plurality of atrial activation events comprises detecting a plurality of P-waves in the sensed electrical cardiac signal.

13. The method of claim 6, wherein detecting the plurality of atrial activation events comprises:
   obtaining a signal indicative of mechanical motion of an atrium; and
   detecting the plurality of atrial activation events based on the signal indicative of mechanical motion of the atrium.

14. The method of claim 1, wherein determining whether intrinsic ventricular activity is occurring comprises:
   beginning a ventricular event detection window;
   incrementing a value of a loss of conduction counter in response to a ventricular sense event not being detected within the ventricular event detection window;
   comparing the value of the loss of conduction counter to a loss of conduction event threshold value; and
   determining intrinsic ventricular activity is occurring in response to determining the value is less than or equal to the loss of conduction event threshold value.

15. The method of claim 1, wherein determining whether intrinsic ventricular activity is occurring comprises:
   detecting, by the processing module and based on the electrical cardiac signal, a ventricular sense event;
   beginning a ventricular activation detection window in response to detecting the ventricular sense event; and
   determining, by the processing module and based on the electrical cardiac signal, a ventricular activation event is detected within the ventricular activation event detection window.

16. The method of claim 15, further comprising:
   incrementing a counter in response to determining no ventricular activation event is detected within the second ventricular activation event detection window;
   comparing a value of the counter to a threshold value; and
   determining intrinsic ventricular activity is occurring in response to determining the value of the counter is less than or equal to the threshold value.

17. The method of claim 16, wherein the threshold value is two, three or four.

18. The method of claim 16, wherein the counter is configured to count a number of cardiac cycles of a predetermined number of cardiac cycles in which no ventricular sense event is detected.

19. The method of claim 16, wherein the counter is configured to count a number of cardiac cycles, within a predetermined time window, in which no ventricular sense event is detected.

20. The method of claim 16, wherein the counter is configured to count a successive number of cardiac cycles in which no ventricular sense event is detected.

21. The method of claim 1, wherein controlling, by the processing module, the leadless pacing device to deliver the ventricular pacing pulse to the patient according to the asynchronous ventricular pacing mode comprises:
   detecting a ventricular activation event;
   determining whether intrinsic depolarization of the ventricle is detected within a detection window that begins at the ventricular activation event; and
   in response to determining that intrinsic depolarization of the ventricle is not detected within the detection window, controlling the leadless pacing device to deliver a pacing pulse to the ventricle.

22. The method of claim 21, wherein detecting the ventricular activation event comprises detecting a plurality of ventricular activation events, the method further comprising determining an average V-V interval based on the plurality of ventricular activation events and controlling the leadless pacing device to deliver pacing pulses according to the asynchronous ventricular pacing mode at a rate equal to the average V-V interval plus an offset.

23. The method of claim 1, wherein detecting atrial oversensing comprises:
   determining a ventricular activation event detection window having a beginning and an end;
   detecting, by the processing module and based on the electrical cardiac signal, the end of a ventricular activation event detection window; and
   detecting, by the processing module and based on the electrical cardiac signal, a plurality of atrial activation events within an atrial activation event detection window that begins at the end of the ventricular activation event detection window.

24. The method of claim 1, wherein determining whether intrinsic ventricular activity is occurring comprises:
   determining a first ventricular activation event detection window having a beginning and an end;
   detecting, by the processing module and based on the electrical cardiac signal, the end of the first ventricular activation event detection window;
   beginning a second ventricular activation detection window in response to detecting the end of the first ventricular activation event detection window; and determining, by the processing module and based on the electrical cardiac signal, a ventricular activation event is detected within the second ventricular activation event detection window.

25. A leadless pacing system comprising:
a leadless pacing device configured to sense an electric cardiac signal and configured to operate in a sensing without pacing mode and an asynchronous ventricular pacing mode; and
a processing module configured to:
   detect atrial oversensing while the leadless pacing device is in a sensing without pacing mode,
   determine, based on the electrical cardiac signal, whether intrinsic ventricular activity is occurring in conjunction with the atrial oversensing,
   when the determined intrinsic ventricular activity is occurring in conjunction with the atrial oversensing, control the leadless pacing device to continue operating in the sensing without pacing mode, and
   when the determined intrinsic ventricular activity is not occurring in conjunction with the atrial oversensing, control the leadless pacing device to deliver a ventricular pacing pulse to the patient according to the asynchronous ventricular pacing mode.

26. The system of claim 25, wherein the system includes an atrial oversensing event counter and the processing module is configured to detect atrial oversensing by at least:
   increment a value of the atrial oversensing event counter to track an atrial oversensing metric;
   comparing the value of the atrial oversensing event counter to an atrial oversensing event threshold value, and
   detecting atrial oversensing in response to determining the value is greater than or equal to the atrial oversensing event threshold value.

27. The system of claim 26, wherein the processor is configured to increment the value of the atrial oversensing event counter to count the number of successive cardiac cycles in which atrial oversensing was detected.

28. The system of claim 26, wherein the processor is configured to increment the value of the atrial oversensing event counter to count the number of cardiac cycles out of a predetermined number of consecutive cardiac cycles in which atrial oversensing was detected.

29. The system of claim 26, wherein the processor is configured to increment the value of the atrial oversensing event counter to count the number of cardiac cycles, within a predetermined period of time, in which atrial oversensing was detected.

30. The system of claim 25, wherein the processing module is configured to detect atrial oversensing by at least:
   detecting, based on the electrical cardiac signal, a ventricular sense event,
   determining an atrial activation event detection window that begins at the ventricular sense event; and
   detecting, based on the electrical cardiac signal, a plurality of atrial activation events within the atrial activation event detection window that begins at the ventricular sense event.

31. The system of claim 30, wherein the system further includes a counter and the processing module is further configured to increment the counter in response to detecting the plurality of atrial activation events within the atrial activation event detection window, compare a value of the counter to a threshold value, and detect atrial oversensing in response to determining the value of the counter is greater than or equal to the threshold value.

32. The system of claim 31, wherein the threshold value is two, three or four.

33. The system of claim 31, wherein the counter is configured to count a number of cardiac cycles in which multiple atrial activation events are detected from among a predetermined number of consecutive cardiac cycles.

34. The system of claim 31, wherein the counter is configured to count a number of cardiac cycles, within a predetermined time window, in which multiple atrial activation events are detected.

35. The system of claim 31, wherein the counter is configured to count a successive number of cardiac cycles in which multiple atrial activation events are detected.

36. The system of claim 30, wherein the processing module is configured to detect the plurality of atrial activation events by at least detecting a plurality of P-waves in the sensed electrical cardiac signal.

37. The system of claim 30, further comprising a motion sensor configured to obtain a signal indicative of mechanical motion of an atrium and wherein the processor is configured to detect the plurality of atrial activation events by at least detecting the plurality of atrial activation events based on the signal indicative of mechanical motion of the atrium.

38. The system of claim 37, wherein the motion sensor comprises an accelerometer.

39. The system of claim 25, wherein the system includes a loss of conduction counter and the processing module is configured to determine whether intrinsic ventricular activity is occurring by at least:
   begin a ventricular event detection window;
   comparing a value of the loss of conduction counter to a loss of conduction event threshold value, the loss of conduction counter being incremented in response to a ventricular sense event not being detected within the ventricular event detection window, and
   determining intrinsic ventricular activity is occurring in response to determining the value is less than or equal to the loss of conduction event threshold value.

40. The system of claim 25, wherein the processing module is configured to determine whether intrinsic ventricular activity is occurring by at least:
   detecting, based on the electrical cardiac signal, a ventricular sense event,
   beginning a ventricular activation detection window in response to detecting the ventricular sense event; and
   determining, based on the electrical cardiac signal, a ventricular activation event is detected within the ventricular activation event detection window.

41. The system of claim 40, wherein the system further includes a counter and the processing module is further configured to increment the counter in response to determining no ventricular activation event is detected within the second ventricular activation event detection window, compare a value of the counter to a threshold value, and determine intrinsic ventricular activity is occurring response to determining the value of the counter is less than or equal to the threshold value.

42. The system of claim 41, wherein the threshold value is two, three or four.

43. The system of claim 41, wherein the counter is configured to count a number of cardiac cycles of a predetermined number of cardiac cycles in which no ventricular sense event is detected.

44. The system of claim 41, wherein the counter is configured to count a number of cardiac cycles, within a predetermined time window, in which no ventricular sense event is detected.

45. The system of claim 41, wherein the counter is configured to count a successive number of cardiac cycles in which no ventricular sense event is detected.

46. The system of claim 25, wherein the processing module is configured to control the leadless pacing device to deliver the ventricular pacing pulse to the patient according to the asynchronous ventricular pacing mode by at least:
  detecting a ventricular activation event,
  beginning a detection window in response to detecting the ventricular activation event;
  determining whether intrinsic depolarization of the ventricle is detected within the detection window that begins at the ventricular activation event, and
  in response to determining that intrinsic depolarization of the ventricle is not detected within the detection window, controlling the leadless pacing device to deliver a pacing pulse to the ventricle.

47. The system of claim 25, wherein the processing module is configured to detect a plurality of ventricular activation events, determine an average V-V interval based on the plurality of ventricular activation events, control the leadless pacing device to deliver pacing pulses according to the asynchronous ventricular pacing mode at a rate equal to the average V-V interval plus an offset.

48. The system of claim 25, wherein the processing module is configured to detect atrial oversensing by at least:
  determining a ventricular activation event detection window having a beginning and an end;
  detecting, based on the electrical cardiac signal, the end of a ventricular activation event detection window; and
  detecting, based on the electrical cardiac signal, a plurality of atrial activation events within an atrial activation event detection window that begins at the end of the ventricular activation event detection window.

49. The system of claim 25, wherein the processing module is configured to determine whether intrinsic ventricular activity is occurring by at least:
  determining a first ventricular activation event detection window having a beginning and an end;
  detecting, based on the electrical cardiac signal, the end of the first ventricular activation event detection window,
  beginning a second ventricular activation detection window in response to detecting the end of the first ventricular activation event detection window; and
  determining, based on the electrical cardiac signal, a ventricular activation event is detected within the second ventricular activation event detection window.

50. A leadless pacing device configurable to operate in a sensing without pacing mode and an asynchronous ventricular pacing mode, the leadless pacing device comprising:
  means for sensing an electrical cardiac signal;
  means for detecting atrial oversensing while the leadless pacing device is in a sensing without pacing mode;
  means for determining, based on the electrical cardiac signal, whether intrinsic ventricular activity is occurring in conjunction with the atrial oversensing;
  means for controlling the leadless pacing device to continue operating in the sensing without pacing mode when the determined intrinsic ventricular activity is occurring in conjunction with the atrial oversensing; and
  means for controlling the leadless pacing device to deliver a ventricular pacing pulse to the patient according to the asynchronous ventricular pacing mode when the determined intrinsic ventricular activity is not occurring in conjunction with the atrial oversensing.

51. The device of claim 50, further comprising counting means, wherein the means for detecting atrial oversensing compares a value of the counting means to an atrial oversensing event threshold value, and detects atrial oversensing in response to determining the value is greater than or equal to the atrial oversensing event threshold value.

52. A non-transitory computer-readable storage medium comprising instructions that, when executed by a processing module of a leadless pacing device configurable to operate in a sensing without pacing mode and an asynchronous ventricular pacing mode, cause the processing module to:
  sense an electrical cardiac signal;
  detect atrial oversensing while the leadless pacing device is in a sensing without pacing mode;
  determine, based on the electrical cardiac signal, whether intrinsic ventricular activity is occurring in conjunction with the atrial oversensing;
  when the determined intrinsic ventricular activity is occurring in conjunction with the atrial oversensing, control the leadless pacing device to continue operating in the sensing without pacing mode; and
  when the determined intrinsic ventricular activity is not occurring in conjunction with the atrial oversensing, control the leadless pacing device to deliver a ventricular pacing pulse to the patient according to the asynchronous ventricular pacing mode.

* * * * *